United States Patent
Furst et al.

(10) Patent No.: US 8,740,973 B2
(45) Date of Patent: Jun. 3, 2014

(54) POLYMER BIODEGRADABLE MEDICAL DEVICE

(75) Inventors: Joseph G. Furst, Lyndhurst, OH (US); William G. Brodbeck, South Euclid, OH (US)

(73) Assignee: ICON Medical Corp., Altanta, GA (US)

( * ) Notice: Subject to any disclaimer, the term of this patent is extended or adjusted under 35 U.S.C. 154(b) by 2525 days.

(21) Appl. No.: 11/337,225

(22) Filed: Jan. 20, 2006

(65) Prior Publication Data

US 2006/0193892 A1      Aug. 31, 2006

Related U.S. Application Data

(63) Continuation-in-part of application No. 10/209,591, filed on Jul. 31, 2002, now abandoned, which is a continuation-in-part of application No. 10/039,816, filed on Oct. 26, 2001, now abandoned, application No. 11/337,225, which is a continuation-in-part of application No. 11/283,434, filed on Nov. 18, 2005, now Pat. No. 8,070,796, which is a continuation-in-part of application No. 11/283,330, filed on Nov. 18, 2005, now Pat. No. 7,967,855.

(60) Provisional application No. 60/658,349, filed on Mar. 3, 2005, provisional application No. 60/629,397, filed on Nov. 19, 2004, provisional application No. 60/658,411, filed on Mar. 3, 2005, provisional application No. 60/629,470, filed on Nov. 19, 2004, provisional application No. 60/658,374, filed on Mar. 3, 2005.

(51) Int. Cl.
A61F 2/06      (2013.01)
A61M 31/00   (2006.01)

(52) U.S. Cl.
USPC ......... 623/1.42; 623/1.15; 623/1.16; 604/509

(58) Field of Classification Search
USPC .................... 623/1.11, 1.15, 1.16, 1.42, 1.46; 604/509
See application file for complete search history.

(56) References Cited

U.S. PATENT DOCUMENTS

| | | |
|---|---|---|
| 4,733,665 A | 3/1988 | Palmaz |
| 4,739,762 A | 4/1988 | Palmaz |
| 4,776,337 A | 10/1988 | Palmaz |

(Continued)

FOREIGN PATENT DOCUMENTS

| | | |
|---|---|---|
| CA | 2172187 | 6/2001 |
| EP | 04330011 A1 | 6/1991 |

(Continued)

OTHER PUBLICATIONS

Microsystems for Drug and Gene Deliver, Michael L. Reed, Senior Member, IEEE and Whye-Kei Lye, Member, IEEE. Proceedings of the IEEE, vol. 92 No. 1, Jan. 2004.

(Continued)

Primary Examiner — Vy Q Bui
(74) Attorney, Agent, or Firm — Fay Sharpe LLP

(57) ABSTRACT

A medical device that is at least partially formed of a biodegradable polymer. The medical device can be at least partially formed by MEMS technology. The medical device can include one or more micro-structures that are also formed by MEMS technology. The medical device can include one or more biological agents that can be controllably and/or uncontrollably released from the medical device,

17 Claims, 7 Drawing Sheets

(56) References Cited

U.S. PATENT DOCUMENTS

| | | | |
|---|---|---|---|
| 4,888,389 A | 12/1989 | Kennedy et al. | |
| 4,942,204 A | 7/1990 | Kennedy | |
| 5,024,671 A | 6/1991 | Tu et al. | |
| 5,051,272 A | 9/1991 | Hermes et al. | |
| 5,059,166 A | 10/1991 | Fischell et al. | |
| 5,067,491 A | 11/1991 | Taylor, II et al. | |
| 5,073,381 A | 12/1991 | Ivan et al. | |
| 5,102,417 A | 4/1992 | Palmaz | |
| 5,108,424 A | 4/1992 | Hoffman, Jr. et al. | |
| 5,180,366 A | 1/1993 | Woods | |
| 5,185,408 A | 2/1993 | Tang et al. | |
| 5,195,984 A | 3/1993 | Schatz | |
| 5,197,977 A | 3/1993 | Hoffman, Jr. et al. | |
| 5,246,452 A | 9/1993 | Sinnot | |
| 5,263,349 A | 11/1993 | Felix et al. | |
| 5,304,121 A | 4/1994 | Sahatjian | |
| 5,306,250 A | 4/1994 | March et al. | |
| 5,316,023 A | 5/1994 | Palmaz | |
| 5,383,928 A | 1/1995 | Scott et al. | |
| 5,437,744 A | 8/1995 | Carlen | |
| 5,443,498 A | 8/1995 | Fontaine | |
| 5,449,382 A | 9/1995 | Dayton | |
| 5,464,650 A | 11/1995 | Berg et al. | |
| 5,500,013 A | 3/1996 | Buscemi et al. | |
| 5,516,781 A | 5/1996 | Morris et al. | |
| 5,545,208 A | 8/1996 | Wolff et al. | |
| 5,556,754 A | 9/1996 | Singer | |
| 5,563,146 A | 10/1996 | Morris et al. | |
| 5,571,170 A | 11/1996 | Palmaz | |
| 5,578,075 A | 11/1996 | Dayton | |
| 5,578,645 A | 11/1996 | Askanazi | |
| 5,605,696 A | 2/1997 | Eury et al. | |
| 5,609,629 A | 3/1997 | Fearnot et al. | |
| 5,616,608 A | 4/1997 | Kinsella et al. | |
| 5,624,411 A | 4/1997 | Tuch | |
| 5,632,840 A | 5/1997 | Campbell | |
| 5,649,977 A | 7/1997 | Campbell | |
| 5,665,728 A | 9/1997 | Morris et al. | |
| 5,679,400 A | 10/1997 | Tuch | |
| 5,695,516 A | 12/1997 | Fischell et al. | |
| 5,716,981 A | 2/1998 | Hunter et al. | |
| 5,725,572 A | 3/1998 | Lam et al. | |
| 5,733,303 A | 3/1998 | Israel et al. | |
| 5,733,925 A | 3/1998 | Kunz et al. | |
| 5,735,871 A | 4/1998 | Sgro | |
| 5,755,781 A | 5/1998 | Jayaraman | |
| 5,772,864 A | 6/1998 | Møller et al. | |
| 5,776,183 A | 7/1998 | Kanesaka et al. | |
| 5,807,944 A | 9/1998 | Hirt et al. | |
| 5,824,045 A | 10/1998 | Alt | |
| 5,824,049 A | 10/1998 | Ragheb et al. | |
| 5,843,172 A | 12/1998 | Yan | |
| 5,849,368 A | 12/1998 | Hostettler et al. | |
| 5,853,419 A | 12/1998 | Imran | |
| 5,861,027 A | 1/1999 | Trapp | |
| 5,879,370 A | 3/1999 | Fischell et al. | |
| 5,911,732 A | 6/1999 | Hojeibane | |
| 5,916,585 A | 6/1999 | Cook | |
| 5,962,620 A | 10/1999 | Reich et al. | |
| 5,964,798 A | 10/1999 | Imran | |
| 5,968,091 A | 10/1999 | Pinchuk et al. | |
| 5,981,568 A | 11/1999 | Kunz et al. | |
| 5,993,972 A | 11/1999 | Reich et al. | |
| 6,007,573 A | 12/1999 | Wallace et al. | |
| 6,059,810 A | 5/2000 | Brown et al. | |
| 6,066,325 A | 5/2000 | Wallace | |
| 6,093,520 A | 7/2000 | Vladimirsky | |
| 6,099,561 A | 8/2000 | Alt | |
| 6,120,536 A | 9/2000 | Ding et al. | |
| 6,146,358 A | 11/2000 | Rowe | |
| 6,156,062 A | 12/2000 | McGuinness | |
| 6,162,247 A | 12/2000 | Weadock et al. | |
| 6,197,013 B1 * | 3/2001 | Reed et al. | 604/509 |
| 6,200,337 B1 | 3/2001 | Moriuchi et al. | |
| 6,200,589 B1 | 3/2001 | Kennedy et al. | |
| 6,200,960 B1 | 3/2001 | Khachigan | |
| 6,206,916 B1 | 3/2001 | Furst | |
| 6,221,099 B1 | 4/2001 | Andersen et al. | |
| 6,240,616 B1 | 6/2001 | Yan | |
| 6,258,121 B1 | 7/2001 | Yang et al. | |
| 6,299,604 B1 | 10/2001 | Ragheb et al. | |
| 6,334,856 B1 * | 1/2002 | Allen et al. | 604/191 |
| 6,335,029 B1 | 1/2002 | Kamath et al. | |
| 6,338,739 B1 * | 1/2002 | Datta et al. | 623/1.15 |
| 6,358,556 B1 | 3/2002 | Ding et al. | |
| 6,365,171 B1 | 4/2002 | Kennedy et al. | |
| 6,365,616 B1 | 4/2002 | Kohn | |
| 6,368,658 B1 | 4/2002 | Schwarz et al. | |
| 6,391,052 B2 | 5/2002 | Buirge et al. | |
| 6,398,863 B1 | 6/2002 | Okinaka et al. | |
| 6,399,144 B2 | 6/2002 | Ding et al. | |
| 6,419,692 B1 | 7/2002 | Yang et al. | |
| 6,436,133 B1 | 8/2002 | Furst et al. | |
| 6,515,009 B1 * | 2/2003 | Kunz et al. | 514/411 |
| 6,517,571 B1 | 2/2003 | Brauker et al. | |
| 6,528,584 B2 | 3/2003 | Kennedy et al. | |
| 6,533,949 B1 | 3/2003 | Yeshurun | |
| 6,555,619 B1 | 4/2003 | Kennedy et al. | |
| 6,558,361 B1 | 5/2003 | Yeshurun | |
| 6,583,251 B1 | 6/2003 | Chaikof et al. | |
| 6,641,611 B2 | 11/2003 | Jayaraman | |
| 6,676,937 B1 * | 1/2004 | Isner et al. | 424/93.7 |
| 6,695,833 B1 | 2/2004 | Frantzen | |
| 6,726,923 B2 | 4/2004 | Lyer et al. | |
| 6,861,406 B2 | 3/2005 | Mascarenhas | |
| 6,887,851 B2 | 5/2005 | Mascarenhas | |
| 6,914,049 B2 | 7/2005 | Mascarenhas | |
| 2001/0013166 A1 | 8/2001 | Yan | |
| 2001/0014717 A1 | 8/2001 | Hossainy et al. | |
| 2002/0032414 A1 | 3/2002 | Ragheb et al. | |
| 2002/0051730 A1 | 5/2002 | Bodnar et al. | |
| 2002/0054900 A1 | 5/2002 | Kamath et al. | |
| 2002/0082679 A1 | 6/2002 | Sirhan et al. | |
| 2002/0095133 A1 | 7/2002 | Gillis et al. | |
| 2002/0098278 A1 | 7/2002 | Bates | |
| 2002/0142974 A1 | 10/2002 | Kohn | |
| 2002/0155737 A1 | 10/2002 | Roy | |
| 2003/0026840 A1 | 2/2003 | Plank et al. | |
| 2003/0040790 A1 | 2/2003 | Furst | |
| 2003/0064098 A1 | 4/2003 | Kararliet et al. | |
| 2003/0068355 A1 | 4/2003 | Shanley et al. | |
| 2003/0083646 A1 | 5/2003 | Sirhan et al. | |
| 2003/0093141 A1 | 5/2003 | DiMatteo et al. | |
| 2003/0099712 A1 | 5/2003 | Jayaraman | |
| 2003/0100499 A1 | 5/2003 | Epstein | |
| 2003/0199969 A1 | 10/2003 | Steinke et al. | |
| 2003/0216534 A1 | 11/2003 | Chaikof et al. | |
| 2003/0228364 A1 | 12/2003 | Nathan | |
| 2003/0229390 A1 | 12/2003 | Ashton | |
| 2003/0229392 A1 | 12/2003 | Wong | |
| 2003/0229393 A1 | 12/2003 | Kutryk et al. | |
| 2004/0072105 A1 | 4/2004 | Yeshurun | |
| 2004/0093076 A1 | 5/2004 | White | |
| 2004/0093077 A1 | 5/2004 | White | |
| 2004/0098014 A1 | 5/2004 | Flugelman | |
| 2005/0029223 A1 | 2/2005 | Yeshurun | |
| 2005/0165358 A1 | 7/2005 | Yeshurun | |
| 2005/0209566 A1 | 9/2005 | Yeshurun | |
| 2005/0271701 A1 | 12/2005 | Cottone et al. | |
| 2006/0051404 A1 | 3/2006 | Yeshurun | |

FOREIGN PATENT DOCUMENTS

| | | |
|---|---|---|
| EP | 734721 | 2/1996 |
| EP | 714640 | 6/1996 |
| EP | 756853 | 2/1997 |
| EP | 0 836839 A2 | 4/1998 |
| EP | 1604697 | 12/2005 |
| WO | WO 93/16176 | 8/1993 |
| WO | WO 99/18998 | 4/1999 |
| WO | WO 99/49907 | 10/1999 |
| WO | WO 99/56663 | 11/1999 |
| WO | WO 00/12175 | 3/2000 |
| WO | WO 00/41649 | 7/2000 |

(56) References Cited

FOREIGN PATENT DOCUMENTS

| | | |
|---|---|---|
| WO | WO 01/17577 | 3/2001 |
| WO | WO 01/41678 | 6/2001 |
| WO | WO 01/45763 | 6/2001 |
| WO | WO 01/97964 | 12/2001 |
| WO | WO 2006/110197 | 10/2006 |

OTHER PUBLICATIONS

Silicon Micromachined Hollow Microneedles for Transdermal Liquid Transport, Jan J.G.E. Gardeniers, Regina Luttge, Erwin J.W. Berenschot, Meint J. De Boer, Shuki Y. Yeshurun, Meir Hefetz, Ronnyb van't Oever, and Abert van den Berg, Journal of Microelectromechanical Systems, vol. 12, No. 6, Dec. 2003.

*Trapidil inhibits Monocyte Chemoattractant Protein-1 and macrophage Accumulation After Balloon Arterial Injury in Rabbits*, Poon M, Cohen J, Siddiqui Z, et al., Lab Invest. 1999; 79:1369-1375.

*The TRAPIST study—A multicentre randomized placebo controlled clinical trial of trapidil for prevention of restenosis after coronary stenting, measured by 3-D intravascular ultrasound*, P.W. Serruys, D.P. Foley, M. Pieper, J.A. de Feyter on behalf of the TRAPIST investigators, European Heart Journal (2001) 22, 1938-1947, doi:10.1053/euhj.2001.2627, available online at http://www.idealibrary.com.

Abstract of *Fast and Reproducible Vascular Neointima Formation in the Hamster Carotid Artery: Effects of Trapidil and Captopril*, Matsuno H, Stassen JM, Hoylaerts MF, Vermylen J, Deckmyn H., Thromb Haemost. Dec. 1995;74(6):1591-6.

*Results of a Meta-Analysis of Trapidil, a PDGF Inhibitor Å A Sufficient Reason for a Second Look to the Pharmacological Approach to Restenosis*, Serruys PW, Banz K, Darcis T, Mignot A, van Es GA, Schwicker D., J Invasive Cardiol. Oct. 1997;9(8):505-512.

*Management of restenosis after Coronary Intervention*, Dangas G, Fuster V., Am Heart J. Aug. 1996;132(2 Pt 1):428-36.

*-New Aspects in Antithrombotic Therapy-Platelet Inhibitors-*, Terres W, Meinertz T., Herz. Feb. 1996;21(1):1-11.

*A Randomized Comparison of Trapidil (triazolopyrimidine), a Platelet-Derived Growth Factor Antagonist, Versus Aspirin in Prevention of Angiographic Restenosis after Coronary Artery Palmaz-Schatz Stent Implantation*, Galassi AR, Tamburino C, Nicosia A, Russo G, Grassi R, Monaco A, Giuffrida G., Catheter Cardiovasc Interv. Feb. 1999;46(2):162-8.

*Reference Chart Derived From Post-Stent-Implantation Intravascular Ultrasound Predictors of 6-Month Expected Restenosis on Quantitative Coronary Angiography*, P. J. de Feyter, P. Kay, C. Disco, and P. W. Serruys, Circulation, Oct. 1999; 100: 1777-1783.

Abstract of *Trapidil in Preventing Restenosis After Balloon Angioplasty in the Ather Osclerotic Rabbit*, MW Liu, GS Roubin, KA Robinson, AJ Black, JA Hearn, RJ Siegel, and SB King, 3d Circulation 1990 81: 1089-1093.

Abstract of *Effects of Trapidil (Triazolopyrimidine), a Platelet-Derived Growth Factor Antagonist, in Preventing Restenosis After Percutaneous Transluminal Coronary Angioplasty*, Okamoto S, Inden M, Setsuda M, Konishi T, Nakano T, Am Heart J. Jun. 1992;123(6):1439-44.

Abstract of *Trapidil (triazolopyrimidine), A Platelet-Derived Growth Factor Antagonist, Reduces Restenosis After Percutaneous Transluminal Coronary Angioplasty. Results of the Randomized, Double-Blind STARC Study. Studio Trapidil Versus Aspirin Nella Restenosi Coronarica*, A Maresta, M Balducelli, L Cantini, A Casari, R Chioin, M Fabbri, A Fontanelli, PA Monici Preti, S Repetto, and S De Serv, Circulation, Dec. 1994; 90: 2710-2715.

Abstract of *The Trapidil Restenosis Trial (STARC study): Background, Methods and Clinical Characteristics of the Patient Population*, Maresta A, Balducelli M, Cantini L, Casari A, Chioin R, Fontanelli A, Monici Preti PA, Repetto S, Raffaghello S.,Clin Trials Metaanal. Apr. 1994;29(1):31-40.

Abstract of *Pharmacological Properties of Trapidil: Comparison with Other Coronary Vasodilators*, Ohnishi H, Kosuzume H, Yamaguchi K, Sato M, Umehara S, Funato H, Itoh C, Suzuki K, Kitamura Y, Suzuki Y, Itoh R., Nippon Yakurigaku Zasshi. Sep. 1980;76(6):495-503.

Abstract of *Effects of Trapidil on Thromboxane A2-induced Aggregation of Platelets, Ischemic Changes in Heart and Biosynthesis of Thromboxane A2*, Ohnishi H, Kosuzume H, Hayashi Y, Yamaguchi K, Suzuki Y, Itoh R., Prostaglandins Med. Mar. 1981;6(3):269-81.

Abstract of *Antithromobitic Activity and the Mechanism of Action of Trapidil (Rocornal)*, Suzuki Y, Yamaguchi K, Shimada S, Kitamura Y, Ohnishi H., Prostaglandins Leukot Med. Dec. 1982;9(6):685-95.

Abstract of *Suppression of Fibroblast Proliferation In Vitro and of Myointimal Hyperplasia In Vivo by the Triazolopyrimidine, Trapidil*, Tiell ML, Sussman II, Gordon PB, Saunders RN, Artery. 1983;12(1):33-50.

*Influence of Cardiovascular Drugs on Platelet Aggregation*, Forster W, Block HU, Giessler C, Heinroth I, Mentz P, Ponicke K, Rettkowski W, Zehl U., : Adv Myocardiol. 1983;4:539-47.

Trapidil in Preventing Restenosis After Balloon Angioplasty in the Atherosclerotic Rabbit, Liu, et al., *Circulation*, vol. 81, No. 3, Mar. 1990.

DNA Delivery from Polymer Matrices for Tissue Engineering, Shea, et al., *Nature Biotechnology*, vol. 17, Jun. 1999.

Polymeric System for Dual Growth Factor Delivery, Richardson, et al., *Nature Biotechnology*, vol. 19, Nov. 2001.

Controlled Growth Factor Release from Synthetic Extracellular Matrices, Lee, et al., *Nature*, vol. 408, Dec. 21/28, 2000.

*Progress in Cardiovascular Disease*, Sonnenblick, et al., Sep./Oct. 1996.

\* cited by examiner

POLYMER BIODEGRADABLE MEDICAL DEVICE

The present invention claims priority on U.S. Provisional Application Ser. No. 60/658,349 filed Mar. 3, 2005. The present invention is also a continuation-in-part of U.S. patent application Ser. No. 10/209,591 filed Jul. 31, 2002 now abandoned, which in turn is a continuation-in-part of U.S. patent application Ser. No. 10/039,816 filed Oct. 26, 2001 now abandoned. The present invention is also a continuation-in-part of U.S. patent application Ser. No. 11/283,434 filed on Nov. 18, 2005 now U.S Pat. No. 8,070,796 which claims priority on U.S. provisional Application Ser. Nos. 60/629,397 filed Nov. 19, 2004 and 60/658,411 filed Mar. 3, 2005. The present invention is also a continuation-in-part of U.S. patent application Ser. No. 11/283,330 filed on Nov. 18, 2005 now U.S. Pat. No. 7,967,855 which claims priority on U.S. provisional Application Ser. Nos. 60/629,470 filed Nov. 19, 2004 and 60/658,374 filed Mar. 3, 2005.

The invention relates generally to medical devices, and particularly to an implant for use within a body, and more particularly to an expandable graph which is useful in repairing various types of body passageways, and even more particularly to an expandable graph which is useful in repairing blood vessels narrowed or occluded by disease. The medical device at least partially includes a novel biodegradable polymer.

BACKGROUND OF THE INVENTION

Medical treatment of various illnesses or diseases commonly includes the use of one or more medical devices. Two types of medical devices that are commonly used to repair various types of body passageways are an expandable graft or stent, or a surgical graft. These devices have been implanted in various areas of the mammalian anatomy. One purpose of a stent is to open a blocked or partially blocked body passageway. When a stent is used in a blood vessel, the stent is used to open the occluded vessel to achieve improved blood flow which is necessary to provide for the anatomical function of an organ. The procedure of opening a blocked or partially blocked body passageway commonly includes the use of one or more stents in combination with other medical devices such as, but not limited to, an introducer sheath, a guiding catheter, a guide wire, an angioplasty balloon, etc.

Various physical attributes of a stent can contribute directly to the success rate of the device. These physical attributes include radiopacity, hoop strength, radial force, thickness of the metal, dimensions of the metal and the like. Cobalt and chromium alloys and stainless steel are commonly used to form stents. These materials are commonly used since such materials having a known history of safety, effectiveness and biocompatibility. These materials how ever have limited physical performance characteristics as to size, strength, weight, bendability, biostability and radiopacity.

The materials commonly used to form prior stents are biostable materials that remained in the blood vessel long after the stent had achieved its function. As such, the continued presence of the stent in the blood vessel increased the risks associated with thrombosis, in-stent restenosis, vascular narrowing and/or restenosis in the blood vessel at the location of the stent. The presence of the stent in the blood vessel also created a potential obstruction to later medical procedures that attempted to correct problems in a body passageway upstream from the stent. The stent was also prone to fracturing over time, especially when the stent was located in regions exposed to bending (e.g., leg, arms, neck, etc.). The repeated bending of the stent could eventually fatigue the stent, thereby resulting in one or more portions of the stent fracturing and/or becoming loose from the stent. These fractures (e.g., strut fractures, etc.) and/or loose portions of the stent could result in damage to the blood vessel and/or one or more regions of the vascular system downstream of the stent.

The current invention is generally directed to a medical device that is at least partially formed of novel biodegradable or bioabsorbable polymer that enhances one or more of the physical properties of a medical device so as to improve the success rate of such medical device and to overcome several of the past problems associated with such medical devices.

SUMMARY OF THE INVENTION

The previously mentioned shortcomings of prior art medical devices are addressed by the novel medical device of the present invention. The medical device of the present invention is generally directed to a biodegradable device that at least partially dissolves in the body and/or is at least partially absorbed by the body. The medical device in accordance with the present invention can be in the form of many different medical devices such as, but are not limited to, stents, grafts, surgical grafts (e.g., vascular grafts, etc.), orthopedic implants, staples, sheaths, guide wires, balloon catheters, hypotubes, catheters, etc. In one non-limiting embodiment, the medical device is directed for use in a body passageway. As used herein, the term "body passageway" is defined to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, etc.). The techniques employed to deliver the medical device to a treatment area include, but are not limited to, angioplasty, vascular anastomoses, transplantation, implantation, subcutaneous introduction, minimally invasive surgical procedures, interventional procedures, and any combinations thereof. For vascular applications, the term "body passageway" primarily refers to blood vessels and chambers in the heart. The stent can be an expandable stent that is expandable by a balloon and/or other means. The stent can have many shapes and forms. Such shapes can include, but are not limited to, stents disclosed in United States Patent or Publication Nos. U.S. Pat. Nos. 6,206,916; 6,436,133; 2004/0093076 and 2004/0093077; and all the prior art cited in these patents and patent publications. These various designs and configurations of stents in such patents and patent publications are incorporated herein by reference. These various designs and configurations of stents in such patents are incorporated herein by reference. When the medical device is in the form of a stent, the stent is designed to be insertable into a treatment area (e.g., body passageway, etc.) and then expanded in the treatment area to enable better or proper fluid flow through the body passageway. Once the stent has achieved its function, the stent can be formed of a material that at least partially dissolves in and/or is at least partially absorbed by the body over time so that the body passageway is eventually free of one or more portions of the stent. As such, after the stent has at least partially fixed or repaired the block or partially blocked body passageway, the stent can be designed to at least partially dissolve in and/or be at least partially absorbed by the body so that the body passageway is at least partially free of the stent. By at least partially removing the stent from the body passageway, potential problems with thrombosis, in-stent restenosis, vascular narrowing and/or restenosis in the body passageway in and/or around at the treatment location of the stent is reduced or eliminated. Such removal or partial removal of the stent from the body passageway also can result in the complete or partial removal of a potential obstruction in the body passageway for potentially future procedures in the body passageway. The biodegradability of one or more portions of the medical device can also fully or partially solve problems associated with fracturing of one or more portions of the medical device. For instance, when the medical device is the form of a stent that is located in a region subjected to bending (e.g., leg, arms, neck, etc.), the repeated bending may cause one or more portions of the stent to eventually fatigue. Over time, one or more fatigued portions of the stent can fracture and/or become dislodged from the stent. These fractures (e.g., strut fractures, etc.) and/or dislodged portions of the stent can result in damage to the body passageway and/or one or more regions of the body passageways downstream of the stent. The biodegradability of one or more portions of the stent can facilitate in at least partially overcoming this problem since such fractures and/or dislodged sections of the stent can be formed of a material that at least partially degrades over time, thus at least partially removing itself from the body passageway of the patient. The biodegradable material is formulated to at least partially dissolve in the body and/or be at least partially absorbed by the body after some period of time (e.g., one month, one year, ten years, etc.) and/or after one or more events (e.g. microfracture, fracture, break, exposure to one or more forms of electromagnetic radiation, exposure to a certain voltage and/or current, exposure to certain sound waves, exposure to certain chemicals and/or biological agents, etc.). As can be appreciated, the stent could be at least partially formed of a material that can be caused to dissolve and/or be bodily absorbed and/or cause accelerated rates of dissolving and/or bodily absorption. In such a situation, the stent could be caused to begin and/or be caused to accelerate in dissolving and/or bodily absorption so as to at least partially remove the stent from a body passageway to enable another medical device to be inserted in the body passageway. As can be appreciated, after the other stent is inserted, a new stent could be reinserted if so needed. As has been illustrated in these few non-limiting examples, there are numerous applications of the medical device of the present invention. It will be appreciated that medical devices other than stents can have many advantages by being partially or fully formed by a biodegradable polymer.

In one non-limiting aspect of the invention, the medical device can be in the form of, but is not limited to, stents, grafts, vascular grafts, valves, orthopedic implants, sheaths, guide wires, balloon catheters, hypotubes, catheters, etc.

In another and/or alternative non-limiting aspect of the invention, the medical device can be designed such that once the medical device has at least partially achieved one or more of its functions, one or more portions of the medical device at least partially dissolves in and/or is at least partially absorbed by the body. The dissolving and/or bodily absorbing of one or more portions of the medical device can occur naturally and/or be activated and/or controlled by one or more events. In one non-limiting example, the natural dissolving and/or bodily absorbing of one or more portions of the medical device can be achieved by the selection of one or more materials that naturally dissolving and/or are bodily absorbed when inserted in a particular portion of a body. As can be appreciated, one or more coatings can be used to control the time period that one or more portions of the medical device begin to dissolve and/or be absorbed and/or substantially completely dissolved and/or absorbed; however, this is not required. In another and/or alternative one non-limiting example, one or more portions of the medical device can be caused to dissolve and/or be absorbed during and/or after exposure to one or more events. Such events include, but are not limited to, microfracture, fracture and/or break in one or more portions of the medical device; exposure of the medical device to one or more forms of electromagnetic radiation; exposure of the medical device to a certain voltage and/or current; exposure of the medical device to certain sound waves; exposure of the medical device to one or more chemicals; and/or exposure of the medical device to one or more biological agents. In one non-limiting example, one or more portions of the medical device are at least partially formed of one or more materials that can be caused to dissolve and/or caused to be absorbed by the body when exposed to one or more forms of electromagnetic radiation (e.g., x-rays, infrared, ultraviolet, microwaves, etc.), a certain voltage and/or current, to certain sound waves (e.g., ultrasonic sound waves, etc.), to one or more chemicals, and/or to one or more biological agents. In one non-limiting design, one or more portions of the medical device are formed or and/or are coated with one or more materials that begin and/or accelerate in dissolving and/or being bodily absorbed when exposed to one or more forms of electromagnetic radiation, to a certain voltage and/or current, to certain sound waves, to one or more chemicals, and/or to one or more biological agents. In another and/or alternative non-limiting example, one or more portions of the medical device are at least partially formed of one or more materials that begin and/or accelerate in dissolving and/or are bodily absorption when one or more portions of the medical device microfracture, fracture and/or break. In one non-limiting design, one or more portions of the medical device are coated with one or more materials that are biostable or slowly dissolve and/or are bodily absorbed. When one or more portions of the medical device microfracture, fracture and/or break, the one or more materials under the coating material is formulated to have a higher rate of dissolving and/or bodily absorption, thus the microfracture, fracture and/or break results in acceleration of one or more portions of the medical device to dissolve and/or bodily adsorb.

In a further and/or alternative non-limiting aspect of the present invention, the medical device can be in the form of a stent. The stent can have a variety of applications such as, but not limited to placement into the vascular system, esophagus, trachea, colon, biliary tract, or urinary tract; however, the stent can have other applications. The stent can have one or more body members, wherein each body member includes first and second ends and a wall surface disposed between the first and second ends. Each body member can have a first cross-sectional area which permits delivery of the body member into a body passageway, and a second, expanded cross-sectional area. The expansion of the stent body member can be accomplished in a variety of manners. Typically, the body member is expanded to its second cross-sectional area by a radially, outwardly extending force applied at least partially from the interior region of the body member (e.g., by use of a balloon, etc.); however, this is not required. When the second cross-sectional area is variable, the second cross-sectional area is typically dependent upon the amount of radially outward force applied to the body member. The stent can be designed such that the body member expands while retaining the original length of the body member; however, this is not required. The body member can have a first cross-sectional shape that is generally circular so as to form a substantially tubular body member; however, the body member can have other cross-sectional shapes. When the stent includes two or more body members, the two or more body members can be connected together by at least one connector member. The stent can include rounded, smooth and/or blunt surfaces to minimize and/or prevent damage to a body passageway as the stent is inserted into a body passageway and/or expanded in a body passageway; however, this is not required. The stent can be treated with gamma, beta and/or e-beam radiation, and/or otherwise sterilized; however, this is not required. The stent can have multiple sections. The sections of the stent can have a uniform architectural configuration, or can have differing architectural configurations. Each of the sections of the stent can be formed of a single part or formed of multiple parts which have been attached. When a section is formed of multiple parts, typically the section is formed into one continuous piece; however, this is not required.

In yet another and/or alternative non-limiting aspect of the present invention, the medical device is at least partially made of one or more polymers that are biodegradable (i.e., dissolves, degrades, is bodily absorbed, or any combination thereof in the body). The biodegradable polymer can form a portion of the medical device or the complete medical device. Generally, at least about 10 weight percent of the medical device includes one or more biodegradable polymers. In one example, at least about 30 weight percent of the medical device includes one or more biodegradable polymers. In another example, at least about 50 weight percent of the medical device includes one or more biodegradable polymers. In another example, at least about 70 weight percent of the medical device includes one or more biodegradable polymers. In another example, at least about 90 weight percent of the medical device includes one or more biodegradable polymer. In another example, the complete medical device can be formed of one or more biodegradable polymers. It can also be appreciated that one or more materials coated on and/or impregnated in the medical device can be biodegradable or biostable. Such other materials can include, but are not limited to, polymers, fabric, metal materials, marker materials, biological agents, adhesive, etc. In one non-limiting design, the medical device is formed of at least about 50 weight percent biodegradable material, and typically at least about 75 weight percent-biodegradable material. The one or more biodegradable polymers that at least partially form the medical device can be a single polymer or be a combination of different polymers. The one or more biodegradable polymers selected to form one or more portions of the medical device are used to form a medical device having the desired physical characteristics of the medical device to achieve the designed purpose of the medical device (e.g., radial strength, flexibility, tinsel strength, longitudinal lengthening, etc). The one or more biodegradable polymers used to at least partially form the medical device are typically selected to withstand the manufacturing process that is needed to be accomplished in order to produce the medical device. These manufacturing processes can include, but are not limited to, laser cutting, etching, MEMS (e.g., micro-machining, etc.) processes, masking processes, crimping, annealing, drawing, pilgering, electroplating, electro-polishing, chemical polishing, ion beam deposition or implantation, sputter coating, vacuum deposition, molding, melting, adhesive bonding, cutting, extruding, etching, heating, cooling, etc.

In still a further and/or alternative non-limiting aspect of the present invention, one or more portions of the medical device can include, contain and/or be coated with one or more biological agents that are used to facilitate in the success of the medical device and/or treated area. The medical device can include, contain and/or be coated with one or more biological agents. The term "biological agent" includes, but is not limited to, a substance, drug or otherwise formulated and/or designed to prevent, inhibit and/or treat one or more biological problems, and/or to promote the healing in a treated area. Non-limiting examples of biological problems that can be addressed by one or more biological agents include, but are not limited to, viral, fungus and/or bacteria infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; and/or the like. Non-limiting examples of biological agents that can be used include, but are not limited to, 5-Fluorouracil and/or derivatives thereof; 5-Phenylmethimazole and/or derivatives thereof; ACE inhibitors and/or derivatives thereof; acenocoumarol and/or derivatives thereof; acyclovir and/or derivatives thereof; actilyse and/or derivatives thereof; adrenocorticotropic hormone and/or derivatives thereof; adriamycin and/or derivatives thereof; agents that modulate intracellular $Ca_{2+}$ transport such as L-type (e.g., diltiazem, nifedipine, verapamil, etc.) or T-type $Ca_{2+}$ channel blockers (e.g., amiloride, etc.); alpha-adrenergic blocking agents and/or derivatives thereof; alteplase and/or derivatives thereof; amino glycosides and/or derivatives thereof (e.g., gentamycin, tobramycin, etc.); angiopeptin and/or derivatives thereof; angiostatic steroid and/or derivatives thereof; angiotensin II receptor antagonists and/or derivatives thereof; anistreplase and/or derivatives thereof; antagonists of vascular epithelial growth factor and/or derivatives thereof; anti-biotics; anti-coagulant compounds and/or derivatives thereof; anti-fibrosis compounds and/or derivatives thereof; anti-fungal compounds and/or derivatives thereof; anti-inflammatory compounds and/or derivatives thereof; Anti-Invasive Factor and/or derivatives thereof; anti-metabolite compounds and/or derivatives thereof (e.g., staurosporin, trichothecenes, and modified diphtheria and ricin toxins, Pseudomonas exotoxin, etc.); anti-matrix compounds and/or derivatives thereof (e.g., colchicine, tamoxifen, etc.); anti-microbial agents and/or derivatives thereof; anti-migratory agents and/or derivatives thereof (e.g., caffeic acid derivatives, nilvadipine, etc.); anti-mitotic compounds and/or derivatives thereof; anti-neoplastic compounds and/or derivatives thereof; anti-oxidants and/or derivatives thereof; anti-platelet compounds and/or derivatives thereof; anti-proliferative and/or derivatives thereof; anti-thrombogenic agents and/or derivatives thereof; argatroban and/or derivatives thereof; ap-1 inhibitors and/or derivatives thereof (e.g., for tyrosine kinase, protein kinase C, myosin light chain kinase, $Ca_{2+}$/calmodulin kinase II, casein kinase II, etc.); aspirin and/or derivatives thereof; azathioprine and/or derivatives thereof; β-Estradiol and/or derivatives thereof; β-1-anticollagenase and/or derivatives thereof; calcium channel blockers and/or derivatives thereof; calmodulin antagonists and/or derivatives thereof (e.g., $H_7$, etc.); CAPTOPRIL and/or derivatives thereof; cartilage-derived inhibitor and/or derivatives thereof; ChIMP-3 and/or derivatives thereof, cephalosporin and/or derivatives thereof (e.g., cefadroxil, cefazolin, cefaclor, etc.); chloroquine and/or derivatives thereof; chemotherapeutic compounds and/or derivatives thereof (e.g., 5-fluorouracil, vincristine, vinblastine, cisplatin, doxyrubicin, adriamycin, tamocifen, etc.); chymostatin and/or derivatives thereof; CILAZAPRIL and/or derivatives thereof; clopidigrel and/or derivatives thereof; clotrimazole and/or derivatives thereof; colchicine and/or derivatives thereof; cortisone and/or derivatives thereof; coumadin and/or derivatives thereof; curacin-A and/or derivatives thereof; cyclosporine and/or derivatives thereof; cytochalasin and/or derivatives thereof (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.); cytokines and/or derivatives thereof; desirudin and/or derivatives thereof; dexamethazone and/or derivatives thereof; dipyridamole and/or derivatives thereof; eminase and/or derivatives thereof; endothelin and/or derivatives thereof; endothelial growth factor and/or derivatives thereof; epidermal growth factor and/or derivatives thereof; epothilone and/or derivatives thereof; estramustine and/or derivatives thereof; estrogen and/or derivatives thereof; fenoprofen and/or derivatives thereof; fluorouracil and/or derivatives thereof; flucytosine and/or derivatives thereof; forskolin and/or derivatives thereof; ganciclovir and/or derivatives thereof; glucocorticoids and/or derivatives thereof (e.g., dexamethasone, betamethasone, etc.); glycoprotein IIb/IIIa platelet membrane receptor antibody and/or derivatives thereof; GM-CSF and/or derivatives thereof; griseofulvin and/or derivatives thereof; growth factors and/or derivatives thereof (e.g., VEGF; TGF; IGF; PDGF; FGF, etc.); growth hormone and/or derivatives thereof; heparin and/or derivatives thereof; hirudin and/or derivatives thereof; hyaluronate and/or derivatives thereof; hydrocortisone and/or derivatives thereof; ibuprofen and/or derivatives thereof; immunosuppressive agents and/or derivatives thereof (e.g., adrenocorticosteroids, cyclosporine, etc.); indomethacin and/or derivatives thereof; inhibitors of the sodium/calcium antiporter and/or derivatives thereof (e.g., amiloride, etc.); inhibitors of the $IP_3$ receptor and/or derivatives thereof; inhibitors of the sodium/hydrogen antiporter and/or derivatives thereof (e.g., amiloride and derivatives thereof, etc.); insulin and/or derivatives thereof; Interferon alpha 2 Macroglobulin and/or derivatives thereof; ketoconazole and/or derivatives thereof; Lepirudin and/or derivatives thereof; LISINOPRIL and/or derivatives thereof; LOVASTATIN and/or derivatives thereof; marevan and/or derivatives thereof; mefloquine and/or derivatives thereof; metalloproteinase inhibitors and/or derivatives thereof; methotrexate and/or derivatives thereof; metronidazole and/or derivatives thereof; miconazole and/or derivatives thereof; monoclonal antibodies and/or derivatives thereof; mutamycin and/or derivatives thereof; naproxen and/or derivatives thereof; nitric oxide and/or derivatives thereof; nitroprusside and/or derivatives thereof; nucleic acid analogues and/or derivatives thereof (e.g., peptide nucleic acids, etc.); nystatin and/or derivatives thereof; oligonucleotides and/or derivatives thereof; paclitaxel and/or derivatives thereof; penicillin and/or derivatives thereof; pentamidine isethionate and/or derivatives thereof; phenindione and/or derivatives thereof; phenylbutazone and/or derivatives thereof; phosphodiesterase inhibitors and/or derivatives thereof; Plasminogen Activator Inhibitor-1 and/or derivatives thereof; Plasminogen Activator Inhibitor-2 and/or derivatives thereof; Platelet Factor 4 and/or derivatives thereof; platelet derived growth factor and/or derivatives thereof; plavix and/or derivatives thereof; POSTMI 75 and/or derivatives thereof; prednisone and/or derivatives thereof; prednisolone and/or derivatives thereof; probucol and/or derivatives thereof; progesterone and/or derivatives thereof; prostacyclin and/or derivatives thereof; prostaglandin inhibitors and/or derivatives thereof; protamine and/or derivatives thereof; protease and/or derivatives thereof; protein kinase inhibitors and/or derivatives thereof (e.g., staurosporin, etc.); quinine and/or derivatives thereof; radioactive agents and/or derivatives thereof (e.g., Cu-64, Ca-67, Cs-131, Ga-68, Zr-89, Ku-97, Tc-99m, Rh-105, Pd-103, Pd-109, In-111, I-123, I-125, I-131, Re-186, Re-188, Au-198, Au-199, Pb-203, At-211, Pb-212, Bi-212, $H_3P^{32}O_4$, etc.); rapamycin and/or derivatives thereof; receptor antagonists for histamine and/or derivatives thereof; refludan and/or derivatives thereof; retinoic acids and/or derivatives thereof; revasc and/or derivatives thereof; rifamycin and/or derivatives thereof; sense or anti-sense oligonucleotides and/or derivatives thereof (e.g., DNA, RNA, plasmid DNA, plasmid RNA, etc.); seramin and/or derivatives thereof; steroids; seramin and/or derivatives thereof; serotonin and/or derivatives thereof; serotonin blockers and/or derivatives thereof; streptokinase and/or derivatives thereof; sulfasalazine and/or derivatives thereof; sulfonamides and/or derivatives thereof (e.g., sulfamethoxazole, etc.); sulphated chitin derivatives; Sulphated Polysaccharide Peptidoglycan Complex and/or derivatives thereof; $T_{H1}$ and/or derivatives thereof (e.g., Interleukins-2, -12, and -15, gamma interferon, etc.); thioprotese inhibitors and/or derivatives thereof; taxol and/or derivatives thereof (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.); ticlid and/or derivatives thereof; ticlopidine and/or derivatives thereof; tick anti-coagulant peptide and/or derivatives thereof; thioprotese inhibitors and/or derivatives thereof; thyroid hormone and/or derivatives thereof; Tissue Inhibitor of Metalloproteinase-1 and/or derivatives thereof; Tissue Inhibitor of Metalloproteinase-2 and/or derivatives thereof; tissue plasma activators; TNF and/or derivatives thereof, tocopherol and/or derivatives thereof; toxins and/or derivatives thereof; tranilast and/or derivatives thereof; transforming growth factors alpha and beta and/or derivatives thereof; trapidil and/or derivatives thereof; triazolopyrimidine and/or derivatives thereof; vapiprost and/or derivatives thereof; vinblastine and/or derivatives thereof; vincristine and/or derivatives thereof; zidovudine and/or derivatives thereof. As can be appreciated, the biological agent can include one or more derivatives of the above listed compounds and/or other compounds. In one non-limiting embodiment, the biological agent includes, but is not limited to, trapidil, trapidil derivatives, taxol, taxol derivatives (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.), cytochalasin, cytochalasin derivatives (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.), paclitaxel, paclitaxel derivatives, rapamycin, rapamycin derivatives, 5-Phenylmethimazole, 5-Phenylmethimazole derivatives, GM-C SF (granulo-cyte-macrophage colony-stimulating-factor), GM-CSF derivatives, or combinations thereof. The type and/or amount of biological agent included in the medical device and/or coated on the medical device can vary. When two or more biological agents are included in and/or coated on the medical device, the amount of two or more biological agents can be the same or different. The type and/or amount of biological agent included on, in and/or in conjunction with the medical device is generally selected for the treatment of one or more medical treatments. Typically the amount of biological agent included on, in and/or used in conjunction with the medical device is about 0.01-100 ug per $mm^2$; however, other amounts can be used. The amount of two of more biological agents on, in and/or used in conjunction with the medical device can be the same or different. In one non-limiting example, the medical device can be coated with and/or includes one or more biological agents such as, but not limited to, trapidil and/or trapidil derivatives, taxol, taxol derivatives (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.), cytochalasin, cytochalasin derivatives (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.), paclitaxel, paclitaxel derivatives, rapamycin, rapamycin derivatives, 5-Phenylmethimazole, 5-Phenylmethimazole derivatives, GM-CSF (granulo-cyte-macrophage colony-stimulating-factor), GM-CSF derivatives, or combinations thereof. In one non-limiting embodiment of the invention, the medical device can be partially of fully coated with one or more biological agents, impregnated with one or more biological agents to facilitate in the success of a particular medical procedure. The one or more biological agents can be coated on and/or impregnated in the medical device by a variety of mechanisms such as, but not limited to, spraying (e.g., atomizing spray techniques, etc.), dip coating, roll coating, sonication, brushing, plasma deposition, depositing by vapor deposition. In another and/or alternative non-limiting embodiment of the invention, the type and/or amount of biological agent included on, in and/or in conjunction with the medical device is generally selected for the treatment of one or more medical treatments. Typically the amount of biological agent included on, in and/or used in conjunction with the medical device is about 0.01-100 ug per $mm^2$; however, other amounts can be used. The amount of two of more biological agents on, in and/or used in conjunction with the medical device can be the same or different. For instance, one or more biological agents can be coated on, and/or incorporated in one or more portions of the medical device to provide local and/or systemic delivery of one or more biological agents in and/or to a body passageway to a) inhibit or prevent thrombosis, in-stent restenosis, vascular narrowing and/or restenosis after the medical device has been inserted in and/or connected to a body passageway, b) at least partially passivate, remove and/or dissolve lipids, fibroblast, fibrin, etc. in a body passageway so as to at least partially remove such materials and/or to passivate such vulnerable materials (e.g., vulnerable plaque, etc.) in the body passageway in the region of the medical device and/or downstream of the medical device. As can be appreciated, the one or more biological agents can have many other or additional uses. In another and/or alternative non-limiting example, the medical device is coated with and/or includes one or more biological agents such as, but not limited to, trapidil and/or trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In still another and/or alternative non-limiting example, the medical device is coated with and/or includes one or more biological agents such as, but not limited to trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof, and one or more additional biological agents, such as, but not limited to, biological agents associated with thrombolytics, vasodilators, anti-hypertensive agents, anti-microbial or anti-biotic, anti-mitotic, anti-proliferative, anti-secretory agents, non-steroidal anti-inflammatory drugs, immunosuppressive agents, growth factors and growth factor antagonists, antitumor and/or chemotherapeutic agents, anti-polymerases, anti-viral agents, anti-body targeted therapy agents, hormones, anti-oxidants, biologic components, radio-therapeutic agents, radiopaque agents and/or radio-labeled agents. In addition to these biological agents, the medical device can be coated with and/or include one or more biological agents that are capable of inhibiting or preventing any adverse biological response by and/or to the medical device that could possibly lead to device failure and/or an adverse reaction by human or animal tissue. A wide range of biological agents thus can be used.

In a further and/or alternative non-limiting aspect of the present invention, the one or more biological agents on and/or in the medical device, when used on the medical device, can be released in a controlled manner so the area in question to be treated is provided with the desired dosage of biological agent over a sustained period of time. As can be appreciated, controlled release of one or more biological agents on the medical device is not always required and/or desirable. As such, one or more of the biological agents on and/or in the medical device can be uncontrollably released from the medical device during and/or after insertion of the medical device in the treatment area. It can also be appreciated that one or more biological agents on and/or in the medical device can be controllably released from the medical device and one or more biological agents on and/or in the medical device can be uncontrollably released from the medical device. It can also be appreciated that one or more biological agents on and/or in one region of the medical device can be controllably released from the medical device and one or more biological agents on and/or in the medical device can be uncontrollably released from another region on the medical device. As such, the medical device can be designed such that 1) all the biological agent on and/or in the medical device is controllably released, 2) some of the biological agent on and/or in the medical device is controllably released and some of the biological agent on the medical device is non-controllably released, or 3) none of the biological agent on and/or in the medical device is controllably released. The medical device can also be designed such that the rate of release of the one or more biological agents from the medical device is the same or different. The medical device can also be designed such that the rate of release of the one or more biological agents from one or more regions on the medical device is the same or different. Non-limiting arrangements that can be used to control the release of one or more biological agent from the medical device include a) at least partially coat one or more biological agents with one or more polymers, b) at least partially incorporate and/or at least partially encapsulate one or more biological agents into and/or with one or more polymers, c) insert one or more biological agents in pores, passageway, cavities, etc. in the medical device and at least partially coat or cover such pores, passageway, cavities, etc. with one or more polymers, and/or incorporate one or more biological agents in the one or more polymers that at least partially form the medical device. As can be appreciated, other or additional arrangements can be used to control the release of one or more biological agent from the medical device. The one or more polymers used to at least partially control the release of one or more biological agent from the medical device can be porous or non-porous. The one or more biological agents can be inserted into and/or applied to one or more surface structures and/or micro-structures on the medical device, and/or be used to at least partially form one or more surface structures and/or micro-structures on the medical device. As such, the one or more biological agents on the medical device can be 1) coated on one or more surface regions of the medical device, 2) inserted and/or impregnated in one or more surface structures and/or micro-structures, etc. of the medical device, and/or 3) form at least a portion or be included in at least a portion of the structure of the medical device. When the one or more biological agents are coated on the medical device, the one or more biological agents can, but is not required to, 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials. As can be appreciated, many other coating arrangements can be additionally or alternatively used. When the one or more biological agents are inserted and/or impregnated in one or more portions of the medical device, one or more surface structure and/or micro-structures of the medical device, and/or one or more surface structures and/or micro-structures of the medical device, 1) one or more other polymers can be applied at least partially over the one or more surface structure and/or micro-structures, surface structures and/or micro-structures of the medical device, 2) one or more polymers can be combined with one or more biological agents, and/or 3) one or more polymers can be coated over or more portions of the body of the medical device; however, this is not required. As such, the one or more biological agents can be 1) embedded in the structure of the medical device; 2) positioned in one or more surface structure and/or micro-structures of the medical device; 3) encapsulated between two polymer coatings; 4) encapsulated between the base structure and a polymer coating; 5) mixed in the base structure of the medical device that includes at least one polymer coating; or 6) one or more combinations of 1, 2, 3, 4 and/or 5. In addition or alternatively, the one or more coatings of the one or more polymers on the medical device can include 1) one or more coatings of non-porous polymers; 2) one or more coatings of a combination of one or more porous polymers and one or more non-porous polymers; 3) one or more coating of porous polymer, or 4) one or more combinations of options 1, 2, and 3. As can be appreciated different biological agents can be located in and/or between different polymer coating layers and/or on and/or the structure of the medical device. As can also be appreciated, many other and/or additional coating combinations and/or configurations can be used. The concentration of one or more biological agents, the type of polymer, the type and/or shape of surface structure and/or micro-structures in the medical device and/or the coating thickness of one or more biological agents can be used to control the release time, the release rate and/or the dosage amount of one or more biological agents; however, other or additional combinations can be used. As such, the biological agent and polymer system combination and location on the medical device can be numerous. As can also be appreciated, one or more biological agents can be deposited on the top surface of the medical device to provide an initial uncontrolled burst effect of the one or more biological agents prior to 1) the control release of the one or more biological agents through one or more layers of polymer system that include one or more non-porous polymers and/or 2) the uncontrolled release of the one or more biological agents through one or more layers of polymer system. The one or more biological agents and/or polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer and/or layer of biological agent is generally at least about 0.01 µm and is generally less than about 150 µm. In one non-limiting embodiment, the thickness of a polymer layer and/or layer of biological agent is about 0.02-75 µm, more particularly about 0.05-50 µm, and even more particularly about 1-30 µm. When the medical device includes and/or is coated with one or more biological agents such that at least one of the biological agents is at least partially controllably released from the medical device, the need or use of body-wide therapy for extended periods of time can be reduced or eliminated. In the past, the use of body-wide therapy was used by the patient long after the patient left the hospital or other type of medical facility. This body-wide therapy could last days, weeks, months or sometimes over a year after surgery. The medical device of the present invention can be applied or inserted into a treatment area and 1) merely requires reduced use and/or extended use of body wide therapy after application or insertion of the medical device or 2) does not require use and/or extended use of body wide therapy after application or insertion of the medical device. As can be appreciated, use and/or extended use of body wide therapy can be used after application or insertion of the medical device at the treatment area. In one non-limiting example, no body-wide therapy is needed after the insertion of the medical device into a patient. In another and/or alternative non-limiting example, short term use of body-wide therapy is needed or used after the insertion of the medical device into a patient. Such short term use can be terminated after the release of the patient from the hospital or other type of medical facility, or one to two days or weeks after the release of the patient from the hospital or other type of medical facility; however, it will be appreciated that other time periods of body-wide therapy can be used. As a result of the use of the medical device of the present invention, the use of body-wide therapy after a medical procedure involving the insertion of a medical device into a treatment area can be significantly reduced or eliminated.

In another and/or alternative non-limiting aspect of the present invention, controlled release of one or more biological agents from the medical device, when controlled release is desired, can be accomplished by using one or more non-porous polymer layers and/or by use of one or more biodegradable polymers used to at least partially form the medical device; however, other and/or additional mechanisms can be used to controllably release the one or more biological agents. The one or more biological agents can be at least partially controllably released by molecular diffusion through the one or more non-porous polymer layers and/or from the one or more biodegradable polymers used to at least partially form the medical device. When one or more non-porous polymer layers are used, the one or more polymer layers are typically biocompatible polymers; however, this is not required. One or more non-porous polymers can be applied to the medical device without the use of chemical, solvents, and/or catalysts; however, this is not required. In one non-limiting example, the non-porous polymer can be at least partially applied by, but not limited to, vapor deposition and/or plasma deposition. The non-porous polymer can be selected so as to polymerize and cure merely upon condensation from the vapor phase; however, this is not required. The application of the one or more non-porous polymer layers can be accomplished without increasing the temperature above ambient temperature (e.g., 65-90° F.); however, this is not required. The non-porous polymer system can be mixed with one or more biological agents prior to being formed into at least a portion of the medical device and/or be coated on the medical device, and/or be coated on a medical device that previously included one or more biological agents; however, this is not required. The use or one or more non-porous polymers allows for accurate controlled release of the biological agent from the medical device. The controlled release of one or more biological agents through the non-porous polymer is at least partially controlled on a molecular level utilizing the motility of diffusion of the biological agent through the non-porous polymer. In one non-limiting example, the one or more non-porous polymer layers can include, but are not limited to, polyamide, parylene (e.g., parylene C, parylene N) and/or a parylene derivative.

In still another and/or alternative non-limiting aspect of the present invention, controlled release of one or more biological agents from the medical device, when controlled release is desired, can be accomplished by using one or more polymers that form a chemical bond with one or more biological agents. In one non-limiting example, at least one biological agent includes trapidil, trapidil derivative or a salt thereof that is covalently bonded to at least one polymer such as, but not limited to, an ethylene-acrylic acid copolymer. The ethylene is the hydrophobic group and acrylic acid is the hydrophilic group. The mole ratio of the ethylene to the acrylic acid in the copolymer can be used to control the hydrophobicity of the copolymer. The degree of hydrophobicity of one or more polymers can also be used to control the release rate of one or more biological agents from the one or more polymers. The amount of biological agent that can be loaded with one or more polymers may be a function of the concentration of anionic groups and/or cationic groups in the one or more polymers. For biological agents that are anionic, the concentration of biological agent that can be loaded on the one or more polymers is generally a function of the concentration of cationic groups (e.g. amine groups and the like) in the one or more polymer and the fraction of these cationic groups that can ionically bind to the anionic form of the one or more biological agents. For biological agents that are cationic (e.g., trapidil, etc.), the concentration of biological agent that can be loaded on the one or more polymers is generally a function of the concentration of anionic groups (i.e., carboxylate groups, phosphate groups, sulfate groups, and/or other organic anionic groups) in the one or more polymers, and the fraction of these anionic groups that can ionically bind to the cationic form of the one or more biological agents. As such, the concentration of one or more biological agents that can be bound to the one or more polymers can be varied by controlling the amount of hydrophobic and hydrophilic monomer in the one or more polymers, by controlling the efficiency of salt formation between the biological agent, and/or the anionic/cationic groups in the one or more polymers.

In still another and/or alternative non-limiting aspect of the present invention, controlled release of one or more biological agents from the medical device, when controlled release is desired, can be accomplished by using one or more polymers that include one or more induced cross-links. These one or more cross-links can be used to at least partially control the rate of release of the one or more biological agents from the one or more polymers. The cross-linking in the one or more polymers can be instituted by a number of techniques such as, but not limited to, using catalysts, using radiation, using heat, and/or the like. The one or more cross-links formed in the one or more polymers can result in the one or more biological agents to become partially or fully entrapped within the cross-linking, and/or form a bond with the cross-linking. As such, the partially or fully biological agent takes longer to release itself from the cross-linking, thereby delaying the release rate of the one or more biological agents from the one or more polymers. Consequently, the amount of biological agent, and/or the rate at which the biological agent is released from the medical device over time can be at least partially controlled by the amount or degree of cross-linking in the one or more polymers.

In still a further and/or alternative aspect of the present invention, a variety of polymers can be coated on the medical device and/or be used to form at least a portion of the medical device. The one or more polymers can be used on the medical for a variety of reasons such as, but not limited to, 1) forming a portion of the medical device, 2) improving a physical property of the medical device (e.g., improve strength, improve durability, improve biocompatibility, reduce friction, etc.), 3) forming a protective coating on one or more surface structures on the medical device, 4) at least partially forming one or more surface structures on the medical device, and/or 5) at least partially controlling a release rate of one or more biological agents from the medical device. As can be appreciated, the one or more polymers can have other or additional uses on the medical device. The one or more polymers can be porous, non-porous, biostable, biodegradable (i.e., dissolves, degrades, is absorbed, or any combination thereof in the body), and/or biocompatible. When the medical device is coated with one or more polymers, the polymer can include 1) one or more coatings of non-porous polymers; 2) one or more coatings of a combination of one or more porous polymers and one or more non-porous polymers; 3) one or more coatings of one or more porous polymers and one or more coatings of one or more non-porous polymers; 4) one or more coatings of porous polymer, or 5) one or more combinations of options 1, 2, 3 and 4. The thickness of one or more of the polymer layers can be the same or different. When one or more layers of polymer are coated onto at least a portion of the medical device, the one or more coatings can be applied by a variety of techniques such as, but not limited to, vapor deposition and/or plasma deposition, spraying, dip-coating, roll coating, sonication, atomization, brushing and/or the like; however, other or additional coating techniques can be used. The one or more polymers that can be coated on the medical device and/or used to at least partially form the medical device can be polymers that are considered to be biodegradable; polymers that are considered to be biostable; and/or polymers that can be made to be biodegradable and/or biodegradable with modification. Non-limiting examples of polymers that are considered to be biodegradable include, but are not limited to, aliphatic polyesters; poly(glycolic acid) and/or copolymers thereof (e.g., poly(glycolide trimethylene carbonate); poly(caprolactone glycolide)); poly(lactic acid) and/or isomers thereof (e.g., poly-L(lactic acid) and/or poly-D Lactic acid) and/or copolymers thereof (e.g. DL-PLA), with and without additives (e.g. calcium phosphate glass), and/or other copolymers (e.g. poly(caprolactone lactide), poly(lactide glycolide), poly(lactic acid ethylene glycol)); poly(ethylene glycol); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl ester-co-carboxylate carbonate) (and/or other tyrosine derived polycarbonates); poly (iminocarbonate); poly(BPA-iminocarbonate); poly(trimethylene carbonate); poly(iminocarbonate-amide) copolymers and/or other pseudo-poly(amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly (amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/pr copolymers, blends, and/or composites of above. Non-limiting examples of polymers that considered to be biostable include, but are not limited to, parylene; parylene c; parylene f; parylene n; parylene derivatives; maleic anyhydride polymers; phosphorylcholine; poly n-butyl methacrylate (PBMA); polyethylene-co-vinyl acetate (PEVA); PBMA/PEVA blend or copolymer; polytetrafluoroethene (Teflon®) and derivatives; poly-paraphenylene terephthalamide (Kevlar®); poly(ether ether ketone) (PEEK); poly(styrene-b-isobutylene-b-styrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and/or copolymers (e.g., n-butyl-acrylate, n-butyl methacrylate, 2-ethylhexyl acrylate, lauryl-acrylate, 2-hydroxy-propyl acrylate, polyhydroxyethyl, methacrylate/methylmethacrylate copolymers); glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g. polystyrene); poly(vinyl ethers) (e.g. polyvinyl methyl ether); poly(vinyl ketones); poly(vinylidene halides) (e.g. polyvinylidene fluoride, polyvinylidene chloride); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronoflex varieties, bionate varieties); vinyl halide polymers and/or copolymers (e.g. polyvinyl chloride); polyacrylic acid; ethylene acrylic acid copolymer; ethylene vinyl acetate copolymer; polyvinyl alcohol; poly(hydroxyl alkylmethacrylate); Polyvinyl esters (e.g. polyvinyl acetate); and/or copolymers, blends, and/or composites of above. Non-limiting examples of polymers that can be made to be biodegradable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyamide; and/or copolymers, blends, and/or composites of above. As can be appreciated, other and/or additional polymers and/or derivatives of one or more of the above listed polymers can be used. The one or more polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer is generally at least about 0.01 μm and is generally less than about 150 μm; however, other thicknesses can be used. In one non-limiting embodiment, the thickness of a polymer layer and/or layer of biological agent is about 0.02-75 μm, more particularly about 0.05-50 μm, and even more particularly about 1-30 μm. As can be appreciated, other thicknesses can be used. In one non-limiting embodiment, the medical device has a body of which a majority is formed of a biodegradable polymer system and that at least a portion of the body includes and/or is coated with parylene, PLGA, POE, PGA, PLLA, PAA, PEG, chitosan and/or derivatives of one or more of these polymers. In another and/or alternative non-limiting embodiment, the medical device has a body of which a majority is formed of a biodegradable polymer system and that at least a portion of the body includes and/or is coated with a non-porous polymer that includes, but is not limited to, polyamide, parylene c, parylene n and/or a parylene derivative. In still another and/or alternative non-limiting embodiment, the medical device has a body of which a majority is formed of a biodegradable polymer system and that at least a portion of the body includes and/or is coated with poly(ethylene oxide), poly(ethylene glycol), and poly(propylene oxide), polymers of silicone, methane, tetrafluoroethylene (including TEFLON brand polymers), tetramethyldisiloxane, and the like.

In another and/or alternative non-limiting aspect of the present invention, the medical device, when including and/or is coated with one or more biological agents, can include and/or can be coated with one or more biological agents that are the same or different in different regions of the medical device and/or have differing amounts and/or concentrations in differing regions of the medical device. For instance, the medical device can a) be coated with and/or include one or more biological agents on at least one portion of the medical device and at least another portion of the medical device is not coated with and/or includes biological agent; b) be coated with and/or include one or more biological agents on at least one portion of the medical device that is different from one or more biologicals on at least another portion of the medical device; c) be coated with and/or include one or more biological agents at a concentration on at least one portion of the medical device that is different from the concentration of one or more biological agents on at least another portion of the medical device; etc.

In still another and/or alternative non-limiting aspect of the present invention, one or more surfaces of the medical device can be treated to achieve the desired coating properties of the one or more biological agents and one or more polymers coated on and/or incorporated in the medical device. Such surface treatment techniques include, but are not limited to, cleaning, buffing, smoothing, etching (chemical etching, plasma etching, etc.), etc. When an etching process is used, various gasses can be used for such a surface treatment process such as, but not limited to, carbon dioxide, nitrogen, oxygen, Freon, helium, hydrogen, etc. The plasma etching process can be used to clean the surface of the medical device, change the surface properties of the medical device so as to affect the adhesion properties, lubricity properties, etc. of the surface of the medical device. As can be appreciated, other or additional surface treatment processes can be used prior to the coating of one or more biological agents and/or polymers on the surface of the medical device. In one non-limiting manufacturing process, one or more portions of the medical device are cleaned and/or plasma etched; however, this is not required. Plasma etching can be used to clean the surface of the medical device, and/or to form one or more non-smooth surfaces on the medical device to facilitate in the adhesion of one or more coatings of biological agents and/or one or more coatings of polymer on the medical device. The gas for the plasma etching can include carbon dioxide and/or other gasses. Once one or more surface regions of the medical device have been treated, one or more coatings of polymer and/or biological agent can be applied to one or more regions of the medical device. For instance, 1) one or more layers of porous or non-porous polymer can be coated on an outer and/or inner surface of the medical device, 2) one or more layers of biological agent can be coated on an outer and/or interior surface of the medical device, or 3) one or more layers of porous or non-porous polymer that includes one or more biological agents can be coated on an outer and/or interior surface of the medical device. The one or more layers of biological agent can be applied to the medical device by a variety of techniques (e.g., dipping, rolling, brushing, spraying, particle atomization, etc.). One non-limiting coating technique is by an ultrasonic mist coating process wherein ultrasonic waves are used to break up the droplet of biological agent and form a mist of very fine droplets. These fine droplets have an average droplet diameter of about 0.1-3 microns. The fine droplet mist facilitates in the formation of a uniform coating thickness and can increase the coverage area on the medical device.

In still yet another and/or alternative non-limiting aspect of the present invention, one or more portions of the medical device can 1) include the same or different biological agents, 2) include the same or different amount of one or more biological agents, 3) include the same or different polymer coatings, 4) include the same or different coating thicknesses of one or more polymer coatings, 5) have one or more portions of the medical device controllably release and/or uncontrollably release one or more biological agents, and/or 6) have one or more portions of the medical device controllably release one or more biological agents and one or more portions of the medical device uncontrollably release one or more biological agents.

In yet another and/or alternative non-limiting aspect of the invention, the medical device can include a marker material that facilitates enabling the medical device to be properly positioned in a body passageway. The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, infrared waves, ultraviolet waves, etc.). In one non-limiting embodiment, the marker material is visible to x-rays (i.e., radiopaque). The marker material can form all or a portion of the medical device and/or be coated on one or more portions (flaring portion and/or body portion; at ends of medical device; at or near transition of body portion and flaring section; etc.) of the medical device. The location of the marker material can be on one or multiple locations on the medical device. The size of the one or more regions that include the marker material can be the same or different. The marker material can be spaced at defined distances from one another so as to form ruler-like markings on the medical device to facilitate in the positioning of the medical device in a body passageway. The marker material can be a rigid or flexible material. The marker material can be a biostable or biodegradable material. When the marker material is a rigid material, the marker material is typically formed of a metal material (e.g., metal band, metal plating, etc.); however, other or additional materials can be used. When the marker material is a flexible material, the marker material typically is formed of one or more polymers that are marker materials in-of-themselves and/or include one or more metal powders and/or metal compounds. In one non-limiting embodiment, the flexible marker material includes one or more metal powders in combinations with parylene, PLGA, POE, PGA, PLLA, PAA, PEG, chitosan and/or derivatives of one or more of these polymers. In another and/or alternative non-limiting embodiment, the flexible marker material includes one or more metals and/or metal powders of aluminum, barium, bismuth, cobalt, copper, chromium, gold, iron, stainless steel, titanium, vanadium, nickel, zirconium, niobium, lead, molybdenum, platinum, yttrium, calcium, rare earth metals, rhenium, zinc, silver, depleted radioactive elements, tantalum and/or tungsten; and/or compounds thereof. The marker material can be coated with a polymer protective material; however, this is not required. When the marker material is coated with a polymer protective material, the polymer coating can be used to 1) at least partially insulate the marker material from body fluids, 2) facilitate in retaining the marker material on the medical device, 3) at least partially shielding the marker material from damage during a medical procedure and/or 4) provide a desired surface profile on the medical device. As can be appreciated, the polymer coating can have other or additional uses. The polymer protective coating can be a biostable polymer or a biodegradable polymer (e.g., degrades and/or is absorbed). The coating thickness of the protective coating polymer material, when used, is typically less than about 300 microns; however, other thickness can be used. In one non-limiting embodiment, the protective coating materials include parylene, PLGA, POE, PGA, PLLA, PAA, PEG, chitosan and/or derivatives of one or more of these polymers.

In a further and/or alternative non-limiting aspect of the present invention, the medical device or one or more regions of the medical device can be constructed by use of one or more microelectromechanical manufacturing techniques (MEMS (e.g., micro-machining, laser micro-machining, laser micro-machining, micro-molding, etc.); however, other or additional manufacturing techniques can be used. The medical device can include one or more surface structures (e.g., pore, channel, pit, rib, slot, notch, bump, teeth, well, hole, groove, etc.). These structures can be at least partially formed by MEMS (e.g., micro-machining, etc.) technology and/or other types of technology. The medical device can include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the medical device. Non-limiting examples of structures that can be formed on the medical devices such as stents are illustrated in United States Patent Publication Nos. 2004/0093076 and 2004/0093077, which are incorporated herein by reference. Typically, the micro-structures, when formed, extend from or into the outer surface no more than about 400 microns, and more typically less than about 300 microns, and more typically about 15-250 microns; however, other sizes can be used. The micro-structures can be clustered together or disbursed throughout the surface of the medical device. Similar shaped and/or sized micro-structures and/or surface structures can be used, or different shaped and/or sized micro-structures can be used. When one or more surface structures and/or micro-structures are designed to extend from the surface of the medical device, the one or more surface structures and/or micro-structures can be formed in the extended position and/or be designed so as to extend from the medical device during and/or after deployment of the medical device in a treatment area. The micro-structures and/or surface structures can be designed to contain and/or be fluidly connected to a passageway, cavity, etc.; however, this is not required. The one or more surface structures and/or micro-structures can be used to engage and/or penetrate surrounding tissue or organs once the medical device has been positioned on and/or in a patient; however, this is not required. The one or more surface structures and/or micro-structures can be used to facilitate in forming or maintaining a shape of a medical device (i.e., see devices in United States Patent Publication Nos. 2004/0093076 and 2004/0093077). The one or more surface structures and/or micro-structures can be at least partially formed by MEMS (e.g., micro-machining, laser micro-machining, micro-molding, etc.) technology; however, this is not required. In one non-limiting embodiment, the one or more surface structures and/or micro-structures can be at least partially formed of a biological agent and/or be formed of a polymer. One or more of the surface structures and/or micro-structures can include one or more internal passageways that can include one or more materials (e.g., biological agent, polymer, etc.); however, this is not required. The one or more surface structures and/or micro-structures can be formed by a variety of processes (e.g., machining, chemical modifications, chemical reactions, MEMS (e.g., micro-machining, etc.), etching, laser cutting, etc.). The one or more coatings and/or one or more surface structures and/or micro-structures of the medical device can be used for a variety of purposes such as, but not limited to, 1) increasing the bonding and/or adhesion of one or more biological agents, adhesives, marker materials and/or polymers to the medical device, 2) changing the appearance or surface characteristics of the medical device, and/or 3) controlling the release rate of one or more biological agents. The one or more micro-structures and/or surface structures can be biostable, biodegradable, etc. One or more regions of the medical device that are at least partially formed by microelectromechanical manufacturing techniques can be biostable, biodegradable, etc. The medical device or one or more regions of the medical device can be at least partially covered and/or filled with a protective material so as to at least partially protect one or more regions of the medical device, and/or one or more micro-structures and/or surface structures on the medical device from damage. One or more regions of the medical device, and/or one or more micro-structures and/or surface structures on the medical device can be damaged when the medical device is 1) packaged and/or stored, 2) unpackaged, 3) connected to and/or otherwise secured and/or placed on another medical device, 4) inserted into a treatment area, 5) handled by a user, and/or 6) form a barrier between one or more micro-structures and/or surface structures and fluids in the body passageway. As can be appreciated, the medical device can be damaged in other or additional ways. The protective material can be used to protect the medical device and one or more micro-structures and/or surface structures from such damage. The protective material can include one or more polymers previously identified above. The protective material can be 1) biostable and/or biodegradable and/or 2) porous and/or non-porous. In one non-limiting design, the polymer is at least partially biodegradable so as to at least partially expose one or more micro-structure and/or surface structure to the environment after the medical device has been at least partially inserted into a treatment area. In another and/or additional non-limiting design, the protective material includes, but is not limited to, sugar (e.g., glucose, fructose, sucrose, etc.), carbohydrate compound, salt (e.g., NaCl, etc.), parylene, PLGA, POE, PGA, PLLA, PAA, PEG, chitosan and/or derivatives of one or more of these materials; however, other and/or additional materials can be used. In still another and/or additional non-limiting design, the thickness of the protective material is generally less than about 300 microns, and typically less than about 150 microns; however, other thicknesses can be used. The protective material can be coated by one or more mechanisms previously described herein.

In still yet another and/or alternative non-limiting aspect of the present invention, the medical device can include and/or be used with a physical hindrance. The physical hindrance can include, but is not limited to, an adhesive, a sheath, a magnet, tape, wire, string, etc. The physical hindrance can be used to 1) physically retain one or more regions of the medical device in a particular form or profile, 2) physically retain the medical device on a particular deployment device, 3) protect one or more surface structures and/or micro-structures on the medical device, and/or 4) form a barrier between one or more surface regions, surface structures and/or micro-structures on the medical device and the fluids in a body passageway. As can be appreciated, the physical hindrance can have other and/or additional functions. The physical hindrance is typically a biodegradable material; however, a biostable material can be used. The physical hindrance can be designed to withstand sterilization of the medical device; however, this is not required. The physical hindrance can be applied to, included in and/or be used in conjunction with one or more medical devices. Additionally or alternatively, the physical hindrance can be designed to be used with and/or in conjunction with a medical device for a limited period of time and then 1) disengage from the medical device after the medical device has been partially or fully deployed and/or 2) dissolve and/or degrade during and/or after the medical device has been partially or fully deployed; however, this is not required. Additionally or alternatively, the physical hindrance can be designed and be formulated to be temporarily used with a medical device to facilitate in the deployment of the medical device; however, this is not required. In one non-limiting use of the physical hindrance, the physical hindrance is designed or formulated to at least partially secure a medical device to another device that is used to at least partially transport the medical device to a location for treatment. In another and/or alternative non-limiting use of the physical hindrance, the physical hindrance is designed or formulated to at least partially maintain the medical device in a particular shape or form until the medical device is at least partially positioned in a treatment location. In still another and/or alternative non-limiting use of the physical hindrance, the physical hindrance is designed or formulated to at least partially maintain and/or secure one type of medical device to another type of medical instrument or device until the medical device is at least partially positioned in a treatment location. The physical hindrance can also or alternatively be designed and formulated to be used with a medical device to facilitate in the use of the medical device. In one non-limiting use of the physical hindrance, when in the form of an adhesive, can be formulated to at least partially secure a medical device to a treatment area so as to facilitate in maintaining the medical device at the treatment area. For instance, the physical hindrance can be used in such use to facilitate in maintaining a medical device on or at a treatment area until the medical device is properly secured to the treatment area by sutures, stitches, screws, nails, rod, etc; however, this is not required. Additionally or alternatively, the physical hindrance can be used to facilitate in maintaining a medical device on or at a treatment area until the medical device has partially or fully accomplished its objective. The physical hindrance is typically a biocompatible material so as to not cause unanticipated adverse effects when properly used. The physical hindrance can be biostable or biodegradable (e.g., degrades and/or is absorbed, etc.). When the physical hindrance includes or is one or more adhesives, the one or more adhesives can be applied to the medical device by, but is not limited to, spraying (e.g., atomizing spray techniques, etc.), dip coating, roll coating, sonication, brushing, plasma deposition, and/or depositing by vapor deposition, brushing, painting, etc.) on the medical device. The physical hindrance can also or alternatively form at least a part of the medical device. One or more regions and/or surfaces of a medical device can also or alternatively include the physical hindrance. The physical hindrance can include one or more biological agents and/or other materials (e.g., marker material, polymer, etc.); however, this is not required. When the physical hindrance is or includes an adhesive, the adhesive can be formulated to controllably release one or more biological agents in the adhesive and/or coated on and/or contained within the medical device; however, this is not required. The adhesive can also or alternatively control the release of one or more biological agents located on and/or contained in the medical device by forming a penetrable or non-penetrable barrier to such biological agents; however, this is not required. The adhesive can include and/or be mixed with one or more polymers; however, this is not required. The one or more polymers can be used to 1) control the time of adhesion provided by said adhesive, 2) control the rate of degradation of the adhesive, and/or 3) control the rate of release of one or more biological agents from the adhesive and/or diffusing or penetrating through the adhesive layer; however, this is not required. When the physical hindrance includes a sheath, the sheath can be designed to partially or fully encircle the medical device. The sheath can be designed to be physically removed from the medical device after the medical device is deployed to a treatment area; however, this is not required. The sheath can be formed of a biodegradable material that at least partially degrades over time to at least partially expose one or more surface regions, micro-structures and/or surface structures of the medical device; however, this is not required. The sheath can include and/or be at least partially coated with one or more biological agents. The sheath includes one or more polymers; however, this is not required. The one or more polymers can be used for a variety of reasons such as, but not limited to, 1) forming a portion of the sheath, 2) improving a physical property of the sheath (e.g., improve strength, improve durability, improve biocompatibility, reduce friction, etc.), and/or 3 at least partially controlling a release rate of one or more biological agents from the sheath. As can be appreciated, the one or more polymers can have other or additional uses on the sheath.

In still another and/or alternative non-limiting aspect of the invention, the medical device can be used in conjunction with one or more other biological agents that are not on the medical device. For instance, the success of the medical device can be improved by infusing, injecting or consuming orally one or more biological agents. Such biological agents can be the same and/or different from the one or more biological agents on and/or in the medical device. Such use of one or more biological agents are commonly used in systemic treatment of a patient after a medical procedure such as body wide therapy after the medical device has been inserted in the treatment area can be reduced or eliminated by use of the novel alloy. Although the medical device of the present invention can be designed to reduce or eliminate the need for long periods of body wide therapy after the medical device has been inserted in the treatment area, the use of one or more biological agents can be used in conjunction with the medical device to enhance the success of the medical device and/or reduce or prevent the occurrence of in-stent restenosis, vascular narrowing, and/or thrombosis. For instance, solid dosage forms of biological agents for oral administration, and/or for other types of administration (e.g., suppositories, etc.) can be used. Such solid forms can include, but are not limited to, capsules, tablets, effervescent tablets, chewable tablets, pills, powders, sachets, granules and gels. The solid form of the capsules, tablets, effervescent tablets, chewable tablets, pills, etc. can have a variety of shapes such as, but not limited to, spherical, cubical, cylindrical, pyramidal, and the like. In such solid dosage form, one or more biological agents can be admixed with at least one filler material such as, but not limited to, sucrose, lactose or starch; however, this is not required. Such dosage forms can include additional substances such as, but not limited to, inert diluents (e.g., lubricating agents, etc.). When capsules, tablets, effervescent tablets or pills are used, the dosage form can also include buffering agents; however, this is not required. Soft gelatin capsules can be prepared to contain a mixture of the one or more biological agents in combination with vegetable oil or other types of oil; however, this is not required. Hard gelatin capsules can contain granules of the one or more biological agents in combination with a solid carrier such as, but not limited to, lactose, potato starch, corn starch, cellulose derivatives of gelatin, etc; however, this is not required. Tablets and pills can be prepared with enteric coatings for additional time release characteristics; however, this is not required. Liquid dosage forms of the one or more biological agents for oral administration can include pharmaceutically acceptable emulsions, solutions, suspensions, syrups, elixirs, etc.; however, this is not required. In one non-limiting embodiment, when at least a portion of one or more biological agents is inserted into a treatment area (e.g., gel form, paste form, etc.) and/or provided orally (e.g., pill, capsule, etc.) and/or anally (suppository, etc.), one or more of the biological agents can be controllably released; however, this is not required. In one non-limiting example, one or more biological agents can be given to a patient in solid dosage form and one or more of such biological agents can be controllably released from such solid dosage forms. In another and/or alternative non-limiting example trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof are given to a patient prior to, during and/or after the insertion of the medical device in a treatment area. Certain types of biological agents may be desirable to be present in a treated area for an extended period of time in order to utilize the full or nearly full clinical potential of the biological agent. For instance, trapidil and/or trapidil derivatives is a compound that has many clinical attributes including, but not limited to, anti-platelet effects, inhibition of smooth muscle cells and monocytes, fibroblast proliferation and increased MAPK-1 which in turn deactivates kinase, a vasodilator, etc. These attributes can be effective in improving the success of a medical device that has been inserted at a treatment area. In some situations, these positive effects of trapidil and/or trapidil derivatives need to be prolonged in a treatment area in order to achieve complete clinical competency. Trapidil and/or trapidil derivatives has a half life in vivo of about 2-4 hours with hepatic clearance of 48 hours. In order to utilize the full clinical potential of trapidil and/or trapidil derivatives, trapidil and/or trapidil derivatives should be metabolized over an extended period of time without interruption; however, this is not required. By inserting trapidil and/or trapidil derivatives in a solid dosage form, the trapidil and/or trapidil derivatives could be released in a patient over extended periods of time in a controlled manner to achieve complete or nearly complete clinical competency of the trapidil and/or trapidil derivatives. In another and/or alternative non-limiting example, one or more biological agents are at least partially encapsulated in one or more polymers. The one or more polymers can be biodegradable, non-biodegradable, porous, and/or non-porous. When the one or more polymers are biodegradable, the rate of degradation of the one or more biodegradable polymers can be used to at least partially control the rate at which one or more biological agents that are released into a body passageway and/or other parts of the body over time. The one or more biological agents can be at least partially encapsulated with different polymer coating thicknesses, different numbers of coating layers, and/or with different polymers to alter the rate at which one or more biological agents are released in a body passageway and/or other parts of the body over time. The rate of degradation of the polymer is principally a function of 1) the water permeability and solubility of the polymer, 2) chemical composition of the polymer and/or biological agent, 3) mechanism of hydrolysis of the polymer, 4) the biological agent encapsulated in the polymer, 5) the size, shape and surface volume of the polymer, 6) porosity of the polymer, 7) the molecular weight of the polymer, 8) the degree of cross-linking in the polymer, 9) the degree of chemical bonding between the polymer and biological agent, and/or 10) the structure of the polymer and/or biological agent. As can be appreciated, other factors may also affect the rate of degradation of the polymer. When the one or more polymers are biostable, the rate at when the one or more biological agents are released from the biostable polymer is a function of 1) the porosity of the polymer, 2) the molecular diffusion rate of the biological agent through the polymer, 3) the degree of cross-linking in the polymer, 4) the degree of chemical bonding between the polymer and biological agent, 5) chemical composition of the polymer and/or biological agent, 6) the biological agent encapsulated in the polymer, 7) the size, shape and surface volume of the polymer, and/or 8) the structure of the polymer and/or biological agent. As can be appreciated, other factors may also affect the rate of release of the one or more biological agents from the biostable polymer. Many different polymers can be used such as, but not limited to, aliphatic polyester compounds (e.g., PLA (i.e. poly(D, L-lactic acid), poly(L-lactic acid)), PLGA (i.e. poly(lactide-co-glycoside), etc.), POE, PEG, PLLA, parylene, chitosan and/or derivatives thereof. As can be appreciated, the at least partially encapsulated biological agent can be introduced into a patient by means other than by oral introduction, such as, but not limited to, injection, topical applications, intravenously, eye drops, nasal spray, surgical insertion, suppositories, intrarticularly, intraocularly, intranasally, intradermally, sublingually, intravesically, intrathecally, intraperitoneally, intracranially, intramuscularly, subcutaneously, directly at a particular site, and the like.

In still another and/or alternative aspect of the invention, the medical device can be an expandable device that can be expanded by use of some other device (e.g., balloon, etc.) and/or is self expanding. The expandable medical device can be fabricated from a material that has no or substantially no shape memory characteristics or can be fabricated from a material having shape-memory characteristics. Typically, when one or more shape-memory materials are used, the shape memory material composition is selected such that the shape memory material remains in an unexpanded configuration at a cold temperature (e.g., below body temperature); however, this is not required. When the shape memory material is heated (e.g., to body temperature) the expandable body section can be designed to expand to at least partially seal and secure the medical device in a body passageway or other region; however, this is not required.

In yet another and/or alternative non-limiting aspect of the invention, the medical device is in the form of a stent. The stent can be an expandable stent that is expandable by a balloon and/or is self-expanding. The material used to form the stent is selected to withstand the manufacturing process that is needed to be accomplished in order to produce the stent. These manufacturing processes can include, but are not limited to, electroplating, MEMS processes, electro-polishing, chemical polishing, ion beam deposition or implantation, sputter coating, vacuum deposition, masking, molding, cutting, etching, and/or other coating processes. The medical device can have one or more body members. The one or more body members can include first and second ends and a wall surface disposed between the first and second ends. Typically, each body member has a first cross-sectional area which permits delivery of the body member into a body passageway, and a second, expanded cross-sectional area. The expansion of one or more body member of the medical device can be accomplished in a variety of manners. In one manner, one or more body members are expanded to the second cross-sectional area by a radially, outwardly extending force applied at least partially from the interior region of the body member (e.g. by use of a balloon, etc.). The body member can include heat sensitive materials (e.g., shape memory materials, etc.) that expand upon exposure to heat, thus not requiring a radially, outwardly extending force applied at least partially from the interior region of the body member; however, such force can be used with such a body member. The second cross-sectional area of the medical device can be fixed or variable. The medical device can be designed such that one or more body members expand while substantially retaining the original longitudinal length of the body member; however, this is not required. The one or more body members can have a first cross-sectional shape that is generally circular so as to form a substantially tubular body member; however, the one or more body members can have other cross-sectional shapes. When the medical device includes two or more body members, the two or more body members can be connected together by at least one connector member. The medical device can include rounded, smooth and/or blunt surfaces to minimize and/or prevent damage to a body passageway as the medical device is inserted into a body passageway and/or expanded in a body passageway; however, this is not required. The medical device can be treated with gamma, beta and/or e-beam radiation, and/or otherwise sterilized; however, this is not required.

In still yet another and/or additional non-limiting aspect of the present invention, one or more portions of the medical device can include or be made of the biological agent and/or polymer. When the medical device is coated with one or more polymers, the polymer can include 1) one or more coatings of non-porous polymers; 2) one or more coatings of a combination of one or more porous polymers and one or more non-porous polymers; 3) one or more coatings of one or more porous polymers and one or more coatings of one or more non-porous polymers; 4) one or more coating of porous polymer, or 5) one or more combinations of options 1, 2, 3 and 4. The thickness of one or more of the polymer layers can be the same or different. Varying types and/or thickness of polymer layers can also be used.

In one non-limiting application of the present invention, there is provided a medical device designed to improve patient procedural outcome. The medical device can have one non-limiting advantage of delivering one or more biological agents into a treatment area (e.g., body passageway, etc.). For instance, the medical device can be designed to be inserted in and/or be connected to a body passageway (e.g., blood vessel, etc.) and which medical device inhibits or prevents thrombosis and/or one or more other diseases. The medical device can be designed to be used as biological agent delivery mechanism to deliver one or more biological agents to and/or into a wall of a body passageway and/or downstream from the site if implantation of the medical device. In one non-limiting design, the medical device is a stent comprised of a base material wherein one or more portions of the base material includes one or more biodegradable polymers. The stent also is coated with and/or includes one or more biological agents. One or more polymers can be used to partially control the release of the biological agent from the medical device; however, this is not required. In one non-limiting controlled release arrangement, molecular diffusion through a polymer is used to control the release rate of one or more biological agents from the medical device When a molecular diffusion mechanism is used, one or more non-porous polymer layers can be used to facilitate in such molecular diffusion; however, this is not required. The molecular composition, molecular structure and/or coating thickness of the non-porous polymer can be selected to control the release rate of one or more biological agents from the medical device.

In another non-limiting application of the present invention, there is provided a medical device that is adapted for introduction into a patient. The medical device can have a variety of applications such as, but not limited to, placement into the vascular system, esophagus, trachea, colon, biliary tract, or urinary tract or used as a replacement for native, synthetic, implanted or engineered organs or vessels. As can be appreciated, the medical device can have other or additional uses. The medical device includes one or more biodegradable polymers. The biodegradable material can be dissolved, absorbed, degraded, or any combination thereof in the body. Various materials that can be used to form one or more portions of the medical device such as, but are not limited to, one or more metals and/or metal alloys (e.g., brass, calcium, carbon, chromium, cobalt, cobalt-chromium alloy, copper, gold, lead, magnesium, molybdenum, molybdenum-rhenium alloy, nickel, Nitinol, platinum, rare earth metals, rhenium, silver, stainless steel, tantalum, tantalum-tungsten alloy, titanium, tungsten, yttrium, zinc zirconium, etc.), fiber materials (e.g., carbon fiber composites, fiberglass, etc.) in combination with and/or polymers (e.g., cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, polytetrafluoroethylene, polylactic acid, polyglycolic acid or copolymers thereof, a polyanhydride, polycaprolactone, polyhydroxy-butyrate valerate or another biodegradable polymer or mixtures or copolymers of these, a protein, an extracellular matrix component, collagen, POE (e.g., Translute™), PEVA, PBMA, PLGA, fibrin, polyethylene tetraphthlate (Dacron), expandable polytetrafluoroethylene (e.g., Gortex, Impra, etc.), polyurethane, etc.). As can be appreciated, the medical device can be completely formed of polymer. One or more biological agents on and/or in the medical device can be released controllably and/or uncontrollably from the medical device. As such, all of the biological agents can be controllably released from the medical device, all of the biological agents can be uncontrollably released from the medical device, or one or more biological agents can be controllably released and one or more biological agents can be uncontrollably released from the medical device. The controlled release of the one or more biological agents from the medical device can be at least partially controlled by molecular diffusion through one or more non-porous polymer layers; however, it will be appreciated that other, or additional mechanism can be used to control the rate of release of one or more biological agents from the medical device. For instance, the one or more biological agents can be selected so as to be chemically bonded to one or more polymers to control the rate of release of one or more biological agents from the medical device; however, this is not required. The one or more polymers can include cross-links to control the rate of release of one or more biological agents from the medical device; however, this is not required. The one or more polymers and/or one or more biological agents can be hydrophobic or hydrophilic, thus can be used to facilitate in the controlled release of the one or more biological agents from the medical device; however, this is not required. The thickness of the one or more polymer layers can be selected to facilitate in the controlled release of the one or more biological agents; however, this is not required. The molecular weight and/or molecular structure of the one or more biological agents and/or one or more polymers can be selected to facilitate in the release of the one or more biological agents; however, this is not required. The medical device can be one or more polymers and/or one or more biological agents. The one or more polymers and/or biological agents can 1) form at least a portion of the medical device, 2) be coated on one or more regions of the medical device, and/or 3) be contained in one or more regions within the medical device. Non-limiting examples of polymers that can be used include parylene, PLGA, POE, PGA, PLLA, PAA, PEG, chitosan and/or derivatives of one or more of these polymers; however, other or additional polymers can be used. Many different biological agents can be used on the medical device. Such biological agents can include, but not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however, it will be appreciated that other or additional biological agents can be used. The structure of the medical device during manufacture can be pretreated to facilitate in the coating of one or more polymers and/or biological agents on the medical device; however, this is not required. The surface topography of the base structure of the medical device can be uniform or varied to achieve the desired operation and/or biological agent released from the medical device. As can be appreciated, one or more regions of the medical device can be constructed by use of one or more microelectromechanical manufacturing techniques; however, this is not required. Materials that can be used by microelectromechanical manufacturing techniques technology include, but are not limited to, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, and chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, and/or a PEG derivative. The medical device can include one or more surface structures, and/or micro-structures that includes one or more biological agents and/or polymers; however, this is not required. These structures can be at least partially formed by MEMS (e.g., micro-machining, etc.) technology and/or other types of technology. The structures can be designed to contain and/or be fluidly connected to a passageway in the medical device that includes one or more biological agents; however, this is not required. The structures can be used to engage and/or penetrate surrounding tissue or organs once the medical device has be position on and/or in a patient; however, this is not required. The structures can be used to at least partially maintain the structure and/or form of the medical device; however, this is not required. One or more polymers and/or biological agents can be inserted in these structures and/or at least partially form these structures of the medical device. The structures can be clustered together or disbursed throughout the surface of the medical device. Similar shaped and/or sized structures can be used, or different shaped and/or sized structures can be used. Typically, the micro-structures, when formed, extend from or into the outer surface no more than about 400 microns, and more typically, less than about 300 microns, and more typically, about 15-250 microns; however, other sizes can be used. The time period one or more biological agents are released from the medical device, when one or more biological agents are used, is typically dependent on the designed medical treatment and/or other factors. In one non-limiting arrangement, one or more biological agents are released from the medical device for at least several days after the medical device is inserted in the body of a patient; however, this is not required. In another one non-limiting arrangement, one or more biological agents are released from the medical device for at least about one week after the medical device is inserted in the body of a patient. In still another one non-limiting arrangement, one or more biological agents are released from the medical device for at least about two weeks after the medical device is inserted in the body of a patient. In yet another one non-limiting arrangement, one or more biological agents are released from the medical device for about one week to one year after the medical device is inserted in the body of a patient. As can be appreciated, the time frame that one or more of the biological agents can be released from the medical device can be longer or shorter. The time period for the release of two or more biological agents from the medical device can be the same or different. The type of the one or more biological agents used on the medical device, the release rate of the one or more biological agents from the medical device, and/or the concentration of the one or more biological agents being released from the medical device can be the same or different. The use of the medical device can be used in conjunction with other biological agents. For instance, the success of the medical device can be enhanced by infusing, injecting or consuming orally the same and/or different biological agent used for anti-platelet and/or anti-coagulation therapy that is being released controllably from the medical device. The introduction of biological agents from a source other than the medical device can have an enhanced or synergistic effect which can improve the success of the medical device. Solid dosage forms of biological agents for oral administration can be used. Such solid forms can include, but are not limited to, capsules, tablets, effervescent tablets, chewable tablets, pills, powders, sachets, granules and gels. In such solid dosage forms, the biological agent can be admixed with at least one filler material such as, but not limited to, sucrose, lactose or starch. Such dosage forms can also comprise, as in normal practice, additional substances such as, but not limited to, inert diluents (e.g., lubricating agents, etc.). When capsules, tablets, effervescent tablets or pills are used, the dosage form can also include buffering agents. Soft gelatin capsules can be prepared to contain a mixture of the biological agent in combination with vegetable oil or other types of oil. Hard gelatin capsules can contain granules of the biological agent in combination with a solid carrier such as, but not limited to, lactose, potato starch, corn starch, cellulose derivatives of gelatin, etc. Tablets and pills can be prepared with enteric coatings for additional time release characteristics. Liquid dosage forms of the biological agent for oral administration can include pharmaceutically acceptable emulsions, solutions, suspensions, syrups, elixirs, etc. Typically the introduction of one or more biological agents used for anti-platelet and/or anti-coagulation therapy from a source other than the medical device is limited to no more than about one day after the medical device has been implanted in a patient, and more typically, no more than about one week after the medical device has been implanted in a patient, and even more typically, no more than about one month after the medical device has been implanted in a patient; however, it can be appreciated that periods of up to 2-3 months or more can be used.

One non-limiting object of the present invention is the provision of a medical device that is at least partially formed of a biodegradable polymer.

Another and/or alternative non-limiting object of the present invention is the provision of a medical device that is at least partially formed by MEMS (e.g., micro-machining, etc.) technology.

Still another and/or alternative non-limiting object of the present invention is the provision of a medical device that is coated and/or impregnated with one or more biological agents.

Yet another and/or alternative object of the present invention is the provision of a medical device that at least partially controls the release rate of one or more biological agents.

Still yet another and/or alternative non-limiting object of the present invention is the provision of a medical device that includes one or more micro-structures on the outer surface of the medical device.

A further and/or alternative non-limiting object of the present invention is the provision of a medical device that improves procedural success rates.

Still a further and/or alternative non-limiting object of the present invention is the provision of a medical device that inhibits or prevents the occurrence of in-stent restenosis, vascular narrowing and/or restenosis after the medical device has been inserted into a body passageway.

Yet a further and/or alternative non-limiting object of the present invention is the provision of a medical device that passivates vulnerable plaque in a body passageway.

These and other advantages will become apparent to those skilled in the art upon the reading and following of this description taken together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE INVENTION

Figure 1:
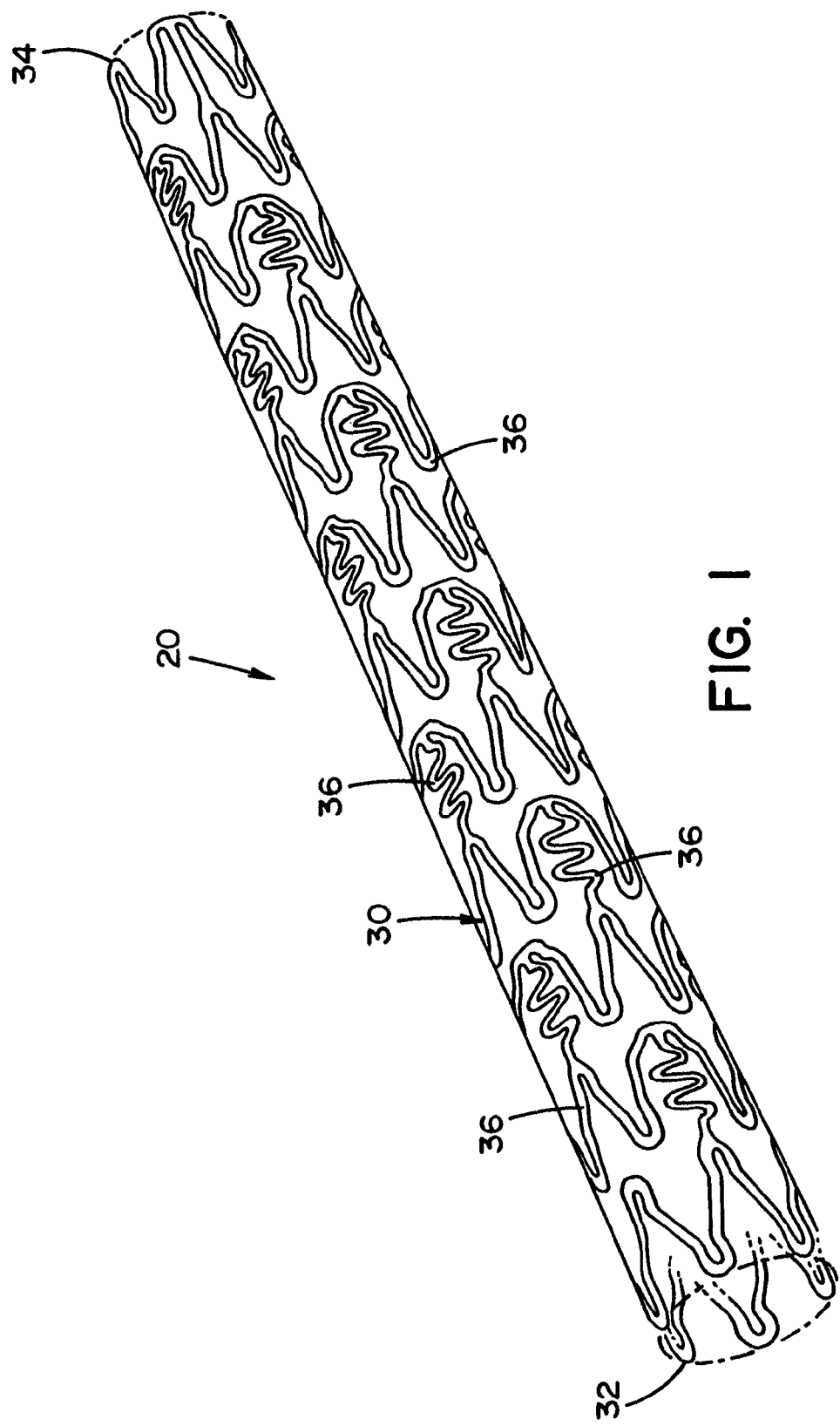
FIG. 1 is a perspective view of a section of a medical device in the form of an unexpanded stent which permits delivery of the stent into a body passageway.

Referring now to the drawings wherein the showings are for the purpose of illustrating embodiments of the invention only and not for the purpose of limiting the same, FIGS. 1-24 disclose a medical device in the form of a stent for use in a body passageway. The stent of the present invention can be at least partially formed of a biodegradeable polymer. The stent of the present invention can at least partially dissolve in the body and/or be absorbed by the body. For instance, the stent can be designed to be insertable in a diseased area in a body passageway and be expanded in the diseased area. Once the stent has at least partially achieved its function, the stent can begin or become completely dissolved in and/or is absorbed by the body naturally and/or in response to one or more events so that the body passageway is at least partially free of the stent. By at least partially removing the stent from the body passageway, problems such as, but not limited to, thrombosis, in-stent restenosis, vascular narrowing and/or restenosis in the body passageway at the location of the stent is reduced or eliminated. Furthermore, the at least partial removal of the stent from the body passageway can result in the removal of a potential obstruction in the body passageway during future procedures in the body passageway. The at least partial biodegradability of the stent can also fully or partially solve problems associated with micro-fracturing, fracturing and/or breaking off of one or more portions of the stent. For instance, when the stent is located in a region that is subject to bending, the repeated bending can eventually fatigue the materials that form the stent. Over time, one or more portions of the stent can micro-fracture, fracture and/or separate from the the stent. These micro-fractures, fractures (e.g., strut fractures, etc.) and/or separated portions of the stent can result in irritation and/or damage to the body passageway and/or one or more regions of the body passageway (e.g., vascular system, etc.) downstream of the stent. The at least partial biodegradability of the stent can overcome this problem since such micro-fractures, fractures and/or separated portions of the stent at least partially degrade and/or are bodily absorbed over time and thus become at least partially removed from the body passageway of the patient. In one specific example, when the medical device is in the form of a stent, the stent can include one or more biological agents that can be used to a) inhibit or prevent thrombosis, in-stent restenosis, vascular narrowing and/or restenosis, and/or b) passivate, remove and/or dissolve passivate plaque, lipids, fibroblasts and/or fibrin in the region of the stent and/or downstream of the stent after the stent has been inserted into the blood vessel.

Figure 2:
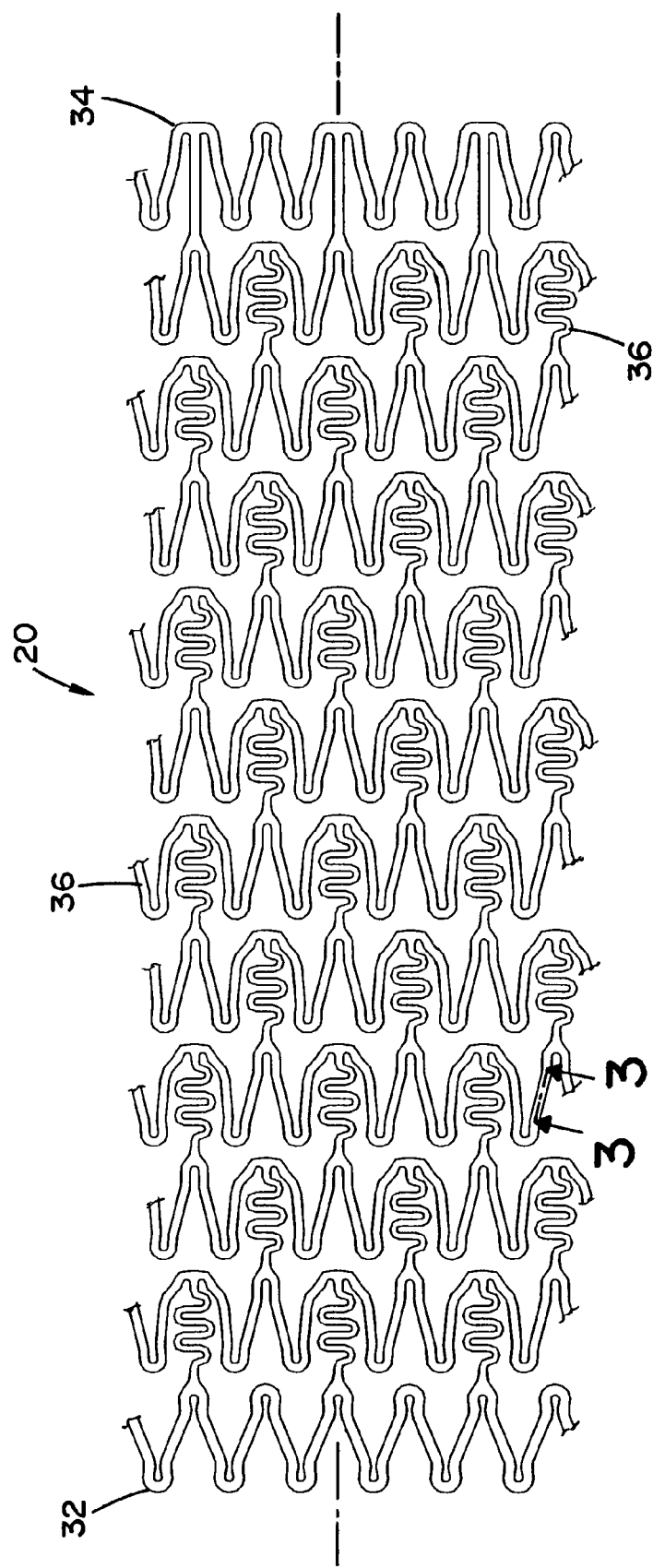
FIG. 2 is a sectional view of the stent of FIG. 1.

The medical device in the form of a stent as illustrated in FIGS. 1 and 2 is designed to be insertable in a diseased area in a body passageway and to expand the diseased area to enable better or proper fluid flow through the body passageway; however, the stent can be used for other or additional reasons. In one specific non-limiting example, the stent can be used to open an obstructed blood vessel. The stent can include and/or be used with one or more biological agents; however, this is not required. When one or more biological agents are used, the one or more biological agents can be used to inhibit thrombosis, in-stent restenosis, vascular narrowing and/or restenosis after the stent has been inserted into the blood vessel; however, this is not required. The one or more biological agents, when used, can also or alternatively be used to remove and/or dissolve lipids, fibroblast, fibrin, etc. from the blood vessel so as to at least partially clean the blood vessel of such substances in the region of the stent and/or downstream of the stent.

Although FIG. 1 illustrates the medical device in the form of a stent for use in the cardiovascular field, the medical device can be in other forms (e.g., vascular graft, sutures, staples, orthopedic implants, nail, rod, screw, etc.) and/or be used in other medical fields (e.g., orthopedic field, cardiology field, pulmonology field, urology field, nephrology field, gastroenterology field, gynecology field, otolaryngology field, etc.). The medical device, when used in the cardiovascular field, can be used to address various medical problems such as, but not limited to, restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications, wounds, myocardial infarction, pulmonary thromboembolism, cerebral thromboembolism, thrombophlebitis, thrombocytopenia and/or bleeding disorders. When the medical device is in the form of a stent, the stent can be expandable such as by a balloon and/or self expanding. The material that is used to form one or more portions of the medical device is typically selected to withstand the manufacturing process used to form the medical device (e.g., electroplating, electro polishing, extrusion, molding, EDM machining, MEMS (e.g., micro-machining, micro-molding, etc.) manufacturing, etching, molding, cutting, chemical polishing, ion beam deposition or implantation, sputter coating, vacuum deposition, plasma deposition, etc.). The medical device can include one or more surface structures and/or micro-structures; however, this is not required. Such structures can be formed by a variety of processes (e.g., machining, chemical modifications, chemical reactions, micro-machining, micro-molding, etching, etc.). The one or more coatings and/or one or more surface structures and/or micro-structures of the medical device, when used, can be used for a variety of purposes such as, but not limited to, 1) increasing the bonding and/or adhesion of one or more biological agents, adhesives, marker materials and/or polymers to the medical device, 2) changing the appearance or surface characteristics of the medical device, and/or 3) controlling the release rate of one or more biological agents. As can be appreciated, other or additional purposes can be achieved. The techniques employed to deliver the medical device include, but are not limited to, angioplasty, vascular anastomoses, transplantation, implantation, subcutaneous introduction, minimally invasive surgical procedures, injection, topical applications, bolus administration, infusion, interventional procedures, and any combinations thereof. When the medical device is in the form of a stent, the medical device can be inserted by techniques such as, but not limited to, balloon delivery, sheath catheter delivery, etc.

Referring again to FIGS. 1-2, there is disclosed a medical device in the form of a stent for a body passageway. The stent is an expandable stent for at least partially expanding occluded segments of a body passageway; however, the stent can have other or additional uses. For example, the expandable stent may be used for, but not limited to, such purposes as 1) a supportive stent for placement within a blocked vasculature opened by transluminal recanalization, which are likely to collapse in the absence of an internal support; 2) forming a catheter passage through the mediastinal and/or other veins occluded by inoperable cancers; 3) reinforcement of catheter created intrahepatic communications between portal and/or hepatic veins in patients suffering from portal hypertension; 4) a supportive stent for placement in the narrowing of the esophagus, the intestine, the ureter and/or the urethra; and/or 5) a supportive stent for reinforcement of reopened and/or previously obstructed bile ducts. Accordingly, use of the term "stent" encompasses the foregoing or other usages within various types of body passageways.

As illustrated in FIG. 1, the medical device 20 in the form of an expandable stent includes at least one tubular shaped body member 30 having a first end 32, a second end 34, and member structures 36 disposed between the first and second ends. FIG. 2 illustrates the stent prior to being formed into a generally tubular shape. As can be appreciated, the stent can be formed of a plurality of body members connected together. Body member 30 has a first diameter which permits delivery of the body member into a body passageway. The first diameter of the body member is illustrated as being substantially constant along the longitudinal length of the body member. As can be appreciated, the body member can have a varying first diameter along at least a portion of the longitudinal length of the body member. The body member also has a second expanded diameter, not shown. The second diameter typically varies in size; however, the second diameter can be non-variable in size. The stent can be expanded in a variety of ways such as by a balloon. A balloon expandable stent is typically pre-mounted or crimped onto an angioplasty balloon catheter. The balloon catheter is then positioned into the patient via a guide wire. Once the stent is properly positioned, the balloon catheter is inflated to the appropriate pressure for stent expansion. After the stent has been expanded, the balloon catheter is deflated and withdrawn, leaving the stent deployed at the treatment area.

Referring again to FIGS. 1-2, the stent can be formed of a variety of materials. The stent is generally is formed of biocompatible materials; however this is not required. The stent is at least partially formed of a polymer material that is biodegradable (i.e., dissolves, degrades, is absorbed, or any combination thereof in the body). A portion or all of the stent can be formed of a biodegradable polymer material. For instance, the body member 30 of stent 20 in FIGS. 1-2 can be fully or partially formed of the biodegradable polymer material. The material or materials used to form the stent include properties (e.g., strength, durability, hardness, biostability, bendability, coefficient of friction, radial strength, flexibility, tensile strength, longitudinal lengthening, stress-strain properties, improved recoil properties, radiopacity, heat sensitivity, biocapatability, etc.) that are selected to form a stent which promotes the success of the stent. The stent can be made of one piece or multiple pieces. The material that is used to form one or more portions of the stent is typically selected to withstand the manufacturing process used to form the stent.

Figure 3:
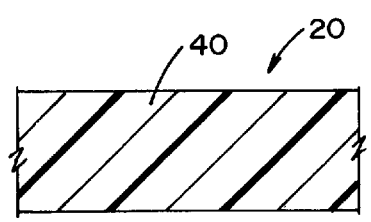
FIG. 3 is a cross-sectional view along line 3-3 of FIG. 2 illustrating a biodegradable material that forms the medical device.

Referring now to FIG. 3, a cross-section of a portion of stent 20 is illustrated which is formed of a biodegradable polymer material 40. The biodegradable polymer can include one or more polymers. Non-limiting examples of biodegradable polymers that can be used include, but are not limited to, aliphatic polyesters; poly(glycolic acid) and/or copolymers thereof (e.g., poly(glycolide trimethylene carbonate); poly (caprolactone glycolide)); poly(lactic acid) and/or isomers thereof (e.g., poly-L(lactic acid) and/or poly-D Lactic acid) and/or copolymers thereof (e.g. DL-PLA), with and without additives (e.g. calcium phosphate glass), and/or other copolymers (e.g. poly(caprolactone lactide), poly(lactide glycolide), poly(lactic acid ethylene glycol)); poly(ethylene glycol); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly (anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl ester-co-carboxylate carbonate) (and/or other tyrosine derived polycarbonates); poly (iminocarbonate); poly(BPA-iminocarbonate); poly(trimethylene carbonate); poly(iminocarbonate-amide) copolymers and/or other pseudo-poly(amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly (amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/or copolymers, blends, and/or composites of above. The selection of the type and/or amount of biodegradable polymer material used to form the stent will generally depend on the particular application of the stent and the desired function of the stent. As can be appreciated, many types of biodegradable polymers can be used to at least partially form the stent. One or more materials (e.g., plasticizer, stabilizing agent, etc.) can be mixed with the one or more polymers to improve the physical properties of the stent. In one non-limiting example, a plasticizer (e.g., triacetin, etc.) can be added to alter the mechanical properties of the stent. As illustrated in FIG. 3, the biodegradable polymer material that is used to form at least a portion of stent 20 does not include any coatings. The surface of the biodegradable polymer material can be treated so as to have generally smooth surfaces. When the surface of the biodegradable polymer material is treated, typically one or more ends of the surfaces are treated by filing, buffing, polishing, grinding, coating, and/or the like to remove or reduce the number of rough and/or sharp surfaces; however, this is not required. The smooth surfaces of the stent can be used to reduce potential damage to surrounding tissue as the stent is positioned in and/or expanded in a body passageway.

Referring now to FIGS. 4-24, the stent can include one or more coatings and/or one or more surface structures and/or micro-structures. The one or more surface structures and/or micro-structures can be formed by a variety of processes (e.g., machining, chemical modifications, chemical reactions, MEMS (e.g., micro-machining, etc.), etching, laser cutting, etc.). The one or more coatings and/or one or more surface structures and/or micro-structures of the stent can be used for a variety of purposes such as, but not limited to, 1) increasing the bonding and/or adhesion of one or more biological agents, adhesives, marker materials and/or polymers to the stent, 2) changing the appearance or surface characteristics of the stent, and/or 3) controlling the release rate of one or more biological agents.

Figure 4:
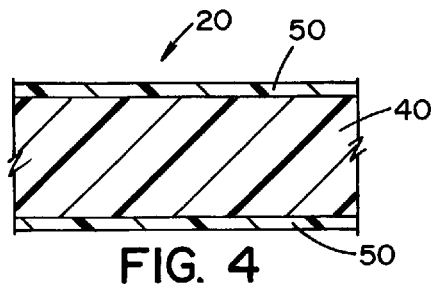
FIG. 4 is a cross-sectional view along line 3-3 of FIG. 2 illustrating the biodegradable material that forms the medical device that includes a polymer coating.

Referring to FIG. 4, the biodegradable polymer material 40 can be coated with a layer 50 of one or more biological agents or polymers that can be used to improve the functionality or success of the stent. The one or more biological agents or polymers. When the stent includes one or more polymer coatings as illustrated in FIG. 4, this polymer coating can be formed of a biodegradable or non-biodegradable material. The one or more polymer coatings can be porous or non-porous polymers. Non-limiting examples of the one or more polymers that can be coated on one or more regions of the biodegradable material 40 include, but are not limited to, parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof. The one or more polymers can be used for a variety of purposes such as, but not limited to, 1) forming a desired surface profile on the surface of the stent, 2) affecting the rate of biodegradability of the stent when inserted in the body passageway, 3) protect the surface of the stent, 4) affecting the coefficient of friction of the surface of the stent, and/or 5) increasing the strength of the stent. As can be appreciated, the one or more polymers can have other or additional functions. The one or more biological agents can include, but are not limited to, anti-biotic agents, anti-body targeted therapy agents, anti-hypertensive agents, anti-microbial agents, anti-mitotic agents, anti-oxidants, anti-polymerases agents, anti-proliferative agents, anti-secretory agents, anti-tumor agents, anti-viral agents, bioactive agents, chemotherapeutic agents, cellular components, cytoskeletal inhibitors, drug, growth factors, growth factor antagonists, hormones, immunosuppressive agents, living cells, non-steroidal anti-inflammatory drugs, radioactive materials, radiotherapeutic agents, thrombolytic agents, vasodilator agents, etc. Non-limiting examples of biological agents that can be used include a vascular active agent that inhibits and/or prevents restenosis, vascular narrowing and/or in-stent restenosis such as, but not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, other or additional biological agents can be included on the stent to improve the functionality or success of the stent. The amount of biological agent delivered to a certain region of a patient's body can be controlled by varying the type of biological agent, the coating thickness of the biological agent, the drug concentration of the biological agent, the solubility of the biological agent, the location of the biological agent that is coated and/or impregnated on and/or in the stent, the amount of surface area of the stent that is coated and/or impregnated with the biological agent, the location of the biological agent on the stent, etc. When the medical device is in the form of a stent for use in the vascular system, the biological agent that is typically included, but not required, on and/or in the stent includes trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however, it will be appreciated that other or additional biological agents can be used. In addition, many other or additional biological agents can be included on and/or in the stent such as, but not limited to, the following categories of biological agents: thrombolytics, vasodilators, anti-hypertensive agents, anti-microbial or anti-biotic, anti-mitotic, anti-proliferative, anti-secretory agents, non-steroidal anti-inflammatory drugs, immunosuppressive agents, growth factors and growth factor antagonists, chemotherapeutic agents, anti-polymerases, anti-viral agents, anti-body targeted therapy agents, hormones, anti-oxidants, radio-therapeutic agents, radiopaque agents and/or radio-labeled agents.

The surface of the biodegradable material 40 can be treated to enhance the coating of the stent and/or to enhance the mechanical characteristics of the stent; however, this is not required. Such surface treatment techniques include, but are not limited to, cleaning, buffing, smoothing, etching (chemical etching, plasma etching, etc.), etc. When an etching process is used, various gasses can be used for such a surface treatment process such as, but not limited to, carbon dioxide, nitrogen, oxygen, Freon, helium, hydrogen, etc. The plasma etching process can be used to clean the surface of the stent, change the surface properties of the stent so as to affect the adhesion properties, lubricity properties, etc. of the surface of the stent. As can be appreciated, other or additional surface treatment processes can be used prior to the coating of one or more biological agents and/or polymers on the surface of the stent.

Referring now to FIGS. 5-8, there is illustrated several non-limiting combinations of biological agent and polymer that have been coated on the surface of the stent. As can be appreciated, other combinations of biological agent and polymer can be used. When one or more biological agents are coated on the stent, the one or more biological agents can be controllably released, uncontrollably released and/or immediately released from the stent to optimize their effects and/or to compliment the function and success of the stent. The controlled release can be accomplished by 1) controlling the size of the surface structures and/or micro-structures on the stent, and/or 2) using one or more polymer coatings; however, other or additional mechanisms can be used to control the release rate of one or more biological agents from the stent. For example, the amount of biological agent delivered to a certain region of a patient's body can be controlled by, but not limited to, one or more of the following: a) selecting the type of biological agent to be used on the stent, b) selecting the amount of biological agent to be used on the stent, c) selecting the coating thickness of the biological agent to be used on the stent, d) selecting the drug concentration of the biological agent to be used on the stent, e) selecting the solubility of the biological agent to be used on the stent, f) selecting the location the biological agent that is to be coated on the stent, g) selecting the amount of surface area of the stent that is coated with the biological agent, h) selecting the location of the biological agent on the stent, i) selecting the size, shape, amount and/or location of the one or more surface structures and/or micro-structures of the stent that include and/or are integrated with the biological agent, j) selecting the type and/or amount of polymer to be mixed with the biological agent, k) selecting the type, amount and/or coating thickness of the polymer coating used to at least partially coat and/or encapsulate the biological agent, etc. As can be appreciated, the amount of one or more biological agent delivered to a region of the body can be at least partially controlled in other or additional ways. The one or more biological agents can be combined with and/or at least partially coated with a polymer that affects the rate at which the biological agent is released from the stent; however, this is not required. The polymer coating can also or alternatively be used to assist in binding the one or more biological agents to the stent; however, this is not required. The polymer coating, when used, can be biodegradable or biostable. The polymer coating can be formulated to form a bond with the biological agent to the stent; however, this is not required. The one or more polymers used in the polymer coating and the one or more biological agents can be mixed together prior to being applied to the stent; however, this is not required. The one or more biological agents that are used in combination with a one or more polymers in the polymer coating can control the release of the biological agent by molecular diffusion; however, this is not required. The thickness of the polymer coating can be about 0.1-25µ; however, other coating thickness can be used. The time period the one or more biological agents are released from the stent can vary. The one or more biological agents, when used, can be coated on the surface of the stent, on the surface of one or more polymer layers; and/or mixed with one or more polymer layers. One or more biological agents can also be coated on the top surface of stent 20. At least one biological agent can be entrapped within and/or coated over with a non-porous polymer layer to at least partially control the release rate of the biological rate; however, this is not required. When a non-porous polymer layer is used on the stent, the non-porous polymer typically includes parylene C, parylene N, parylene F and/or a parylene derivative; however, other or additional polymers can be used. Various coating combinations can be used on the stent. For instance, a polymer layer that includes one or more polymers can be coated on the top of the layer of one or more biological agents; however, this is not required. In another example, the stent 20 can include a layer of one or more polymers. A layer of one or more biological agent can be coated on the top of the layer of one or more polymers; however, this is not required. Furthermore, one or more polymers can be coated on the layer of one or more biological agents; however, this is not required. As can be appreciated other coating combinations can be used. Generally, one or more biological agents are released from the stent for at least several days after the stent is inserted in the body of a patient; however, this is not required. Generally, one or more biological agents are released from the stent for at least about 1-7 days after the stent is inserted in the body of a patient, typically at least about 1-14 days after the stent is inserted in the body of a patient, and more typically about 1-365 days after the stent is inserted in the body of a patient; however, this is not required. As can be appreciated, the time frame that one or more of the biological agents are released from the stent can be shorter or longer. The time period for the release of two or more biological agents from the stent can be the same or different. The type of the one or more biological agents used on the stent, the release rate of the one or more biological agents from the stent, and/or the concentration of the one or more biological agents being released from the stent during a certain time period is typically selected to deliver the one or more biological agents to the area of treatment and/or disease. When the stent is used in the vascular system, the one or more biological agents can be used to inhibit or prevent thrombosis, restenosis, vascular narrowing and/or in-stent restenosis after the stent has been implanted; however, this is not required. When the stent is used in the vascular system, the biological agent that is generally included on and/or in the stent is, but not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however, it will be appreciated that other or additional biological agents can be used. In addition, many other or additional biological agents can be included on and/or in the stent such as, but not limited to, the following categories of biological agents: thrombolytics, vasodilators, anti-hypertensive agents, anti-microbial or anti-biotic, anti-mitotic, anti-proliferative, anti-secretory agents, non-steroidal anti-inflammatory drugs, immunosuppressive agents, growth factors and growth factor antagonists, chemotherapeutic agents, anti-polymerases, anti-viral agents, anti-body targeted therapy agents, hormones, anti-oxidants, radio-therapeutic agents, radiopaque agents and/or radio-labeled agents.

Figure 5:
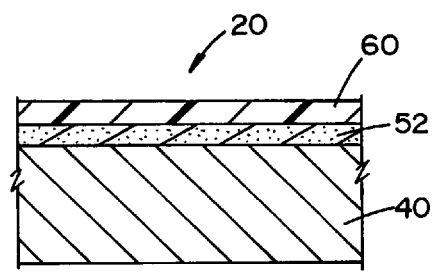
FIG. 5 is a cross-sectional view along line 3-3 of FIG. 2 illustrating one type of coating on a medical device.

Referring now to FIG. 5, the base structure 40 of the stent 20 includes a layer 52 of biological agent. The layer of biological agent can include one or more biological agents. In one non-limiting example, the biological agent includes trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. A polymer layer 60 is coated on the top of layer 52. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more biological agents of layer 52 from stent 20. The one or more non-porous polymers can include, but is not limited to, parylene C, parylene N, parylene F and/or a parylene derivative.

Figure 6:
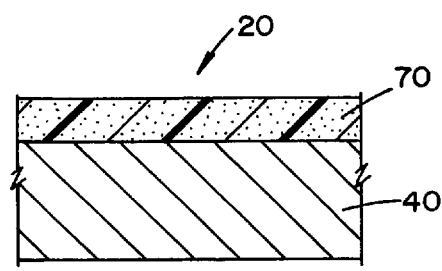
FIG. 6 is a cross-sectional view along line 3-3 of FIG. 2 illustrating another type of coating on a medical device.

As illustrated in FIG. 6, the base structure 40 of stent 20 includes a layer 70 of polymer and biological agent. Layer 70 can include one or more biological agents mixed with one or more polymers. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers can include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers included in layer 70 include a non-porous polymer to at least partially control a rate of release by molecular diffusion of the one or more biological agents in layer 70. The non-porous polymer can include, but is not limited to, parylene C, parylene N, parylene F and/or a parylene derivative.

Figure 7:
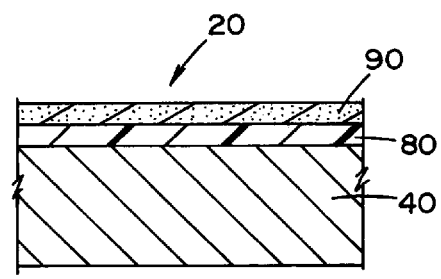
FIG. 7 is a cross-sectional view along line 3-3 of FIG. 2 illustrating another type of coating on a medical device.

As illustrated in FIG. 7, the base structure 40 of stent 20 includes a layer 80 of polymer. Layer 80 can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. The one or more non-porous polymers, when used, can include, but are not limited to, parylene C, parylene N, parylene F and/or a parylene derivative. A layer 90 of one or more biological agents is coated on top of polymer layer 80. Polymer layer 80 can be used to facilitate in the securing of layer 90 to the stent; however, this is not required. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The placement of a layer of biological agent on the top surface of the stent can provide a burst of biological agent in the treatment area (e.g., body passageway, etc.) after insertion of the stent. In one non-limiting example, the one or more biological agents include trapidil and/or derivatives thereof.

Figure 8:
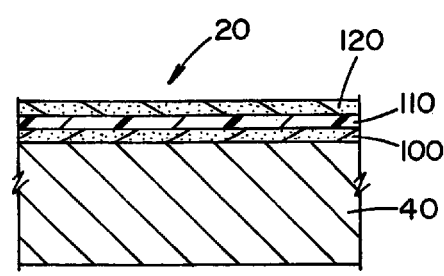
FIG. 8 is a cross-sectional view along line 3-3 of FIG. 2 illustrating another type of coating on a medical device.

As illustrated in FIG. 8, the base structure 40 of stent 20 includes a layer 100 of one or more biological agents. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. A polymer layer 110 is coated on the top of layer 100. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more biological agents of layer 100 from stent 20. The one or more non-porous polymers can include, but are not limited to, parylene C, parylene N, parylene F and/or a parylene derivative. A layer 120 of biological agent is coated on top of polymer layer 110. Layer 120 can include one or more biological agents. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The placement of a layer of biological agent on the top surface of the stent provide can provide a burst of one or more biological agents in the treatment area (e.g., body passageway, etc.) after insertion of the stent. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, other combinations of polymer layer and layer of biological agent can be used on the stent. These other combinations are also encompassed within the scope of the present invention.

Figure 9:
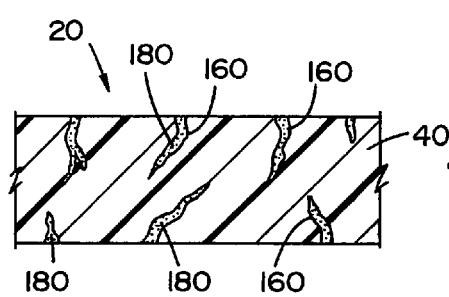
FIGS. 9 and 10 are a cross-sectional view along line 3-3 of FIG. 2 illustrating a biodegradable material that forms a medical device that includes a plurality of two types of pores and/or micro-pores in the biodegradable material which are filled with one or more biological agents.
Figure 10:
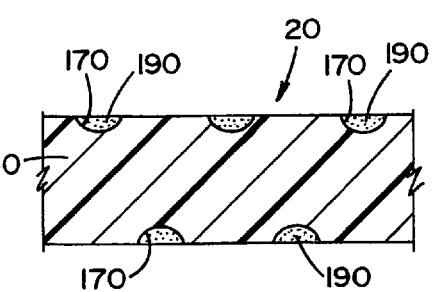

Referring now to FIG. 9, the base structure 40 of stent 20 includes a plurality of surface structures and/or micro-structures 160. The surface structures and/or micro-structures are illustrated as being formed in the base structure of the stent. As defined herein, a micro-structure (e.g., micro-channel, micro-needle, micro-pore, etc.) is a structure that has at least one dimension (e.g., average width, average diameter, average height, average length, average depth, etc.) that is no more than about 2 mm, and typically no more than about 1 mm. The surface structures and/or micro-structures can be formed in the biodegradable material during the formation of the stent and/or from the surface treatment of the stent (e.g. etching, mechanical drill, etc.). In one non-limiting example, the stent is formed by MEMS technology and the surface structures and/or micro-structures are formed by MEMS technology. The surface structures and/or micro-structures are illustrated as being on the form of pores in the biodegradable material. As can be appreciated, many other structures can be formed in the biodegradable material. For instance, as illustrated in FIG. 10, the surface structures and/or micro-structures are in the form of pits or depressions 170. As illustrated in FIGS. 9 and 10, the surface structures and/or micro-structures 160, 170 include one or more biological agents 180, 190; however, it can be appreciated that one or more surface structures and/or micro-structures can include a) a combination of polymer and biological agent, b) only a polymer, c) one biological agent, or d) nothing. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The size of the one or more surface structures and/or micro-structures can be used to at least partially control the rate of release of the biological agent and/or polymer from the one or more surface structures and/or micro-structures; however, this is not required. As can be appreciated, a layer that includes one or more biological agents or a combination of one or more biological agents and one or more polymers, not shown, can be coated in the surface of the biodegradable material; however, this is not required. This coating, if used, can include one or more the same or one or more different biological agents from the one or more biological agents in the surface structures and/or micro-structures. As can also be appreciated, additional coatings of biological agent and/or polymer, not shown, can be used. The polymer, when used, can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer includes one or more non-porous polymers to at least partially control a rate of release by molecular diffusion of the one or more biological agents from stent 20. The one or more non-porous polymers can include, but are not limited to, parylene C, parylene N, parylene F and/or a parylene derivative.

Figure 17:
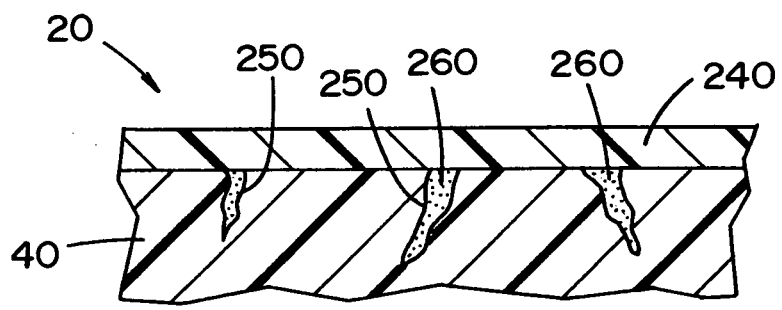
FIG. 17 is a cross-sectional view along line 3-3 of FIG. 2 illustrating a biodegradable material that forms a medical device that includes a plurality of two types of pores and/or micro-pores in the biodegradable material which are filled with one or more biological agents and covered with one or more polymer coatings.

As illustrated in FIG. 17, a polymer layer 240 is coated on the top surface of the biodegradable material 40. The polymer layer 240 covers the one or more biological agents 260 located in the surface structures and/or micro-structures 250. The polymer layer can include one or more polymers. The polymer layer can include a porous polymer and/or non-porous polymer the polymer layer can include one or more biological agent; however, this is not required. The polymer layer can include a biostable and/or biodegradable polymer. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer includes one or more non-porous polymers to at least partially control a rate of release by molecular diffusion of the one or more biological agents from stent 20. The one or more non-porous polymers can include, but are not limited to, parylene C, parylene N, parylene F and/or a parylene derivative. The biological agent can include, but is not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof.

Figure 11:
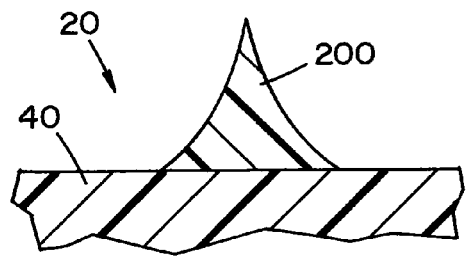
FIGS. 11 and 12 are a cross-sectional view along line 3-3 of FIG. 2 illustrating a biodegradable material that forms a medical device that includes one or more micro-needles on the surface of the stent.
Figure 12:
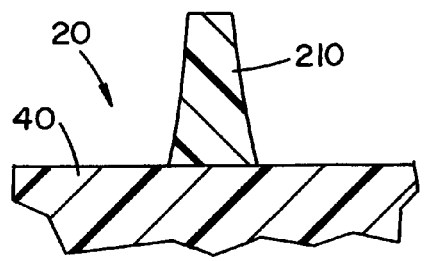
Figure 13:
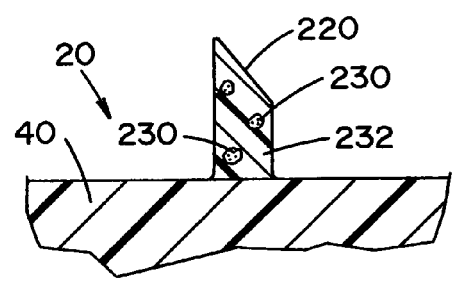
FIG. 13 is a cross-sectional view along line 3-3 of FIG. 2 illustrating a biodegradable material that forms a medical device that includes a plurality of micro-needles on the surface of the stent which are formed of one or more polymers and biological agents.

Referring now to FIGS. 11-13, the biodegradable material 40 of stent 20 includes one or more needles or micro-needles 200, 210, 220 formed on the surface of the stent. These needles or micro-needles can be formed by MEMS (e.g., micro-machining, etc.) technology and/or by other processes. As illustrated in FIGS. 11-13, the needles or micro-needles can have a variety of shapes and sizes. The needles or micro-needles can be at least partially formed from one or more polymers and/or biological agents. It can be appreciated that the needles or micro-needles can be at least partially formed of other of additional material such as, but not limited to one or more adhesives, etc. As illustrated in FIG. 13, the needles or micro-needles include a combination of one or more polymers 232 and/or one or more biological agents 230. As can be appreciated, one or more layer of one or more biological agents and/or polymers can be coated on the needles or micro-needles; however, this is not required. When the one or more needles or micro-needles include and/or are coated with one or more biological agents, such biological agents can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The use of one or more biological agents to coat the top surface of the needles or micro-needles can provide a burst of biological agent in the interior of the blood vessel and/or the blood vessel itself during and/or after insertion of the stent.

Figure 14:
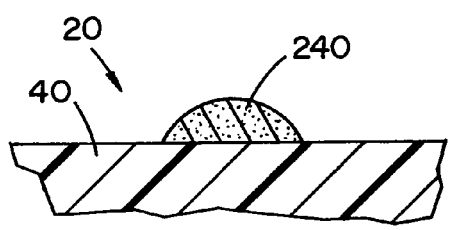
FIG. 14 is a cross-sectional view along line 3-3 of FIG. 2 illustrating a biodegradable material that forms a medical device that includes one or more micro-structures on the surface of the medical device.

Referring now to FIG. 14, the biodegradable material 40 of stent 20 includes one or more surface structures or micro-structures 240 in the form of a mound; however, it can be appreciated that other or additional shapes can be used. The mound is formed on the surface of the stent. The mound can be formed by MEMS (e.g., micro-machining, etc.) technology and/or by other processes. The mound is shown to be formed of one or more biological agents; however, it can be appreciated that the mound can be formed of one or more polymers or a combination of one or more polymers and biological agents. As can also be appreciated, other or additional materials can be used to at least partially form the mound. The one or more biological agents can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however other or additional biological agents can be used. The one or more biological agents used to form the mound can provide a burst of biological agent in the interior of a body passageway and/or the body passageway itself during and/or after insertion of the stent in the body passageway; however, this is not required. As can be appreciated, a layer of one or more polymers can be coated on the mound; however, this is not required. The polymer layer can be used to control the release rate of the one or more biological agents from the mound; however, this is not required. The polymer layer can also or alternatively provide protection to the mound structure; however, this is not required. When the mound includes and/or is coated with one or more polymers, such polymers can include, but are not limited to, parylene, parylene C, parylene N, parylene F, PLGA, PEVA, PLA, PBMA, POE, PGA, PLLA, PAA, PEG, chitosan and/or derivatives of one or more of these polymers.

Figure 15:
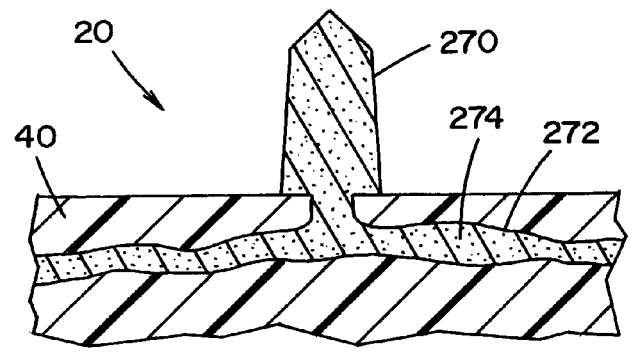
FIG. 15 is a cross-sectional view along line 3-3 of FIG. 2 illustrating a biodegradable material that forms a medical device that includes a plurality of another type of micro-needles on the surface of the biodegradable material which are formed of one or more biological agents and which are interconnected to at least internal channel in the biodegradable material which is filled with one or more biological agents.
Figure 16:
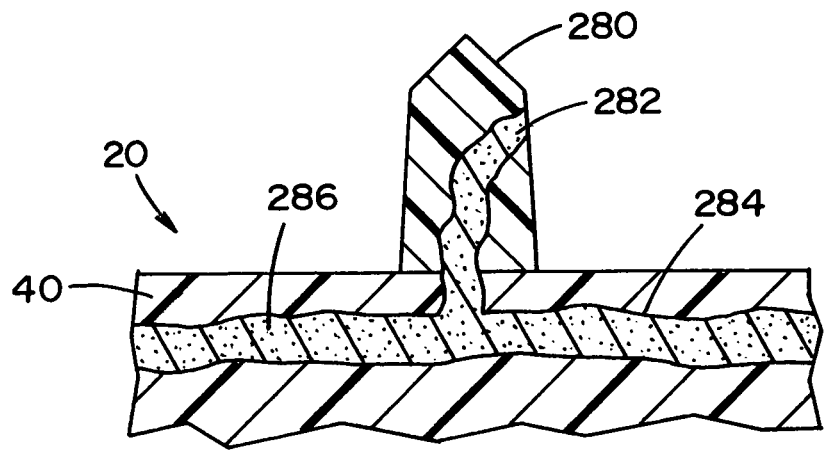
FIG. 16 is a cross-sectional view along line 3-3 of FIG. 2 illustrating a biodegradable material that forms a medical device that includes a plurality of another type of micro-needles on the surface of the biodegradable material which are formed of one or more polymers and which the micro-needles include a channel filled with one or more biological agents and which channel in the micro-needle is interconnected to at least an internal channel in the biodegradable material which is filled with one or more biological agents.
Figure 18:
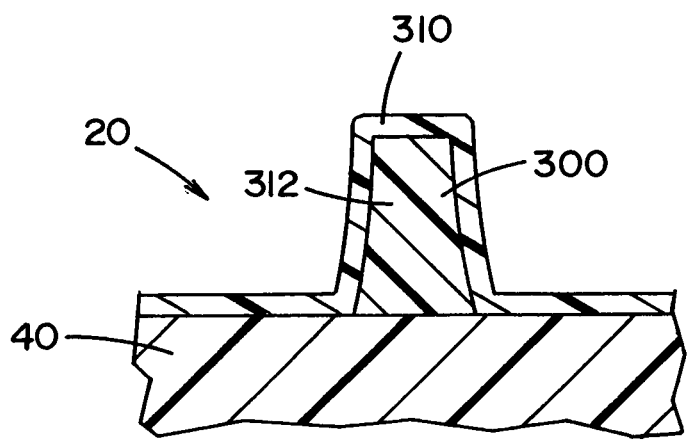
FIG. 18 is a cross-sectional view along line 3-3 of FIG. 2 illustrating one or more micro-needles on the surface of the medical device which one or more micro-needles are formed from one or more polymers and/or biological agents and are coated with one or more polymers and/or biological agents.

Referring now to FIGS. 15, 16 and 18, the biodegradable material 40 of stent 20 includes one or more needles or micro-needles 270, 280, 300. These needles or micro-needles can be formed by MEMS (e.g., micro-machining, etc.) technology and/or by other processes. The one or more needles or micro-needles are formed on the surface of the stent. The one or more needles or micro-needles can formed from one or more biological agents, polymers, and/or adhesives. The polymer can be porous, non-porous, biodegradable and/or biostable. Polymers that can be used to at least partially form the one or more needles or micro-needles include, but are not limited to, Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers; however, other or additional polymers can be used. Non-limiting examples of one or more biological agents that can be used can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however other or additional biological agents can be used.

Referring to FIG. 15, the one or more needles or micro-needles 270 are formed from one or more biological agents. As can be appreciated, a layer of one or more polymers can be coated on the one or more needles or micro-needles, not shown; however, this is not required. The polymer layer can be used to control the release rate of the one or more biological agents from the one or more needles or micro-needles; however, this is not required. The polymer layer can also or alternatively provide protection to the structure of the one or more needles or micro-needles; however, this is not required. When the one or more needles or micro-needles includes and/or is coated with one or more polymers, such polymers can include, but are not limited to, parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof. As illustrated in FIG. 15, the needle or micro-needle is formed over on opening in the surface of the biodegradable material which opening is connected to a surface structure and/or micro-structure 272 in the biodegradable material. The surface structure and/or micro-structure is shown to be a channel; however, other or additional surface structures and/or micro-structures can be included in the biodegradable material. These surface structures and/or micro-structures can be formed by MEMS (e.g., micro-machining, etc.) technology and/or by other processes. The surface structure and/or micro-structure 272 is shown to be filled with one or more biological agents 274; however, it can be appreciated that the surface structures and/or micro-structures can includes other or additional materials (e.g., polymers, adhesive, etc.); however, this is not required. As can also be appreciated, the surface structures and/or micro-structures can be partially or fully empty of any type of material; however, this is not required. The one or more biological agents 274 in the surface structure and/or micro-structure 272 can be the same or different from the one or more biological agents that at least partially form the one or more needles or micro-needles 270.

Referring now to FIG. 16, the biodegradable material 40 of stent 20 includes one or more needles or micro-needles 280. These needles or micro-needles can be formed by MEMS (e.g., micro-machining, etc.) technology and/or by other processes. The one or more needles or micro-needles are formed on the surface of the stent. The one or more needles or micro-needles are formed from one or more polymer. As can be appreciated, the one or more needles or micro-needles also or alternatively be formed from one or more biological agents and/or adhesives. The polymer can be porous, non-porous, biodegradable and/or biostable. Polymers that can be used to at least partially form the one or more needles or micro-needles include, but are not limited to, parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof; however, other or additional polymers can be used. The one or more needles or micro-needles are shown to includes a channel that is filled with one or more biological agents. As can be appreciated, other or additional materials can be included in the channel in the one or more needles or micro-needles (e.g., polymer, adhesive, etc.). As can be appreciated, a layer of one or more polymers can be coated on the one or more needles or micro-needles; however, this is not required. The polymer layer can be used to control the release rate of the one or more biological agents from the one or more needles or micro-needles; however, this is not required. The polymer layer can also or alternatively provide protection to the structure of the one or more needles or micro-needles; however, this is not required. When the one or more needles or micro-needles include and/or are coated with one or more polymers, such polymers can include, but are not limited to, parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof. The surface of the one or more needles or micro-needles can include a layer of one or more biological agents to provide a burst of biological agent in the interior of the body passageway and/or the body passageway itself during and/or after insertion of the stent; however, this is not required. The one or more biological agents that can be used can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however other or additional biological agents can be used. The channel of one or more biological agents 282 in the one or more needles or micro-needles 280 are shown to be connected to an opening in the surface of the biodegradable material which opening is connected to an surface structure and/or micro-structure 284 in the biodegradable material. The surface structure and/or micro-structure is shown to be a channel; however, other or additional surface structures and/or micro-structures can be included in the biodegradable material. These surface structure and/or micro-structures can be formed by MEMS (e.g., micro-machining, etc.) technology and/or by other processes. The surface structure and/or micro-structure 284 is shown to be filled with one or more biological agents 286; however, it can be appreciated that the surface structure and/or micro-structures can includes other or additional materials (e.g., polymers, adhesive, etc.); however, this is not required. As can also be appreciated, the surface structure and/or micro-structures can be partially or fully empty of any type of material; however, this is not required. The one or more biological agents 286 in the surface structure and/or micro-structure 284 can be the same or different from the one or more biological agents 282 in the channel of the one or more needles or micro-needles 280.

Referring now to FIG. 18, one or more needles or micro-needles 300 on biodegradable material 40 of stent 20 are formed from one or more polymers 312. As can be appreciated, the one or more needles or micro-needles can also or alternatively be formed from one or more biological agents and/or adhesives. The polymer can be porous, non-porous, biodegradable and/or biostable. Polymers that can be used to at least partially form the one or more needles or micro-needles include, but are not limited to, parylene, parylene C, parylene N, parylene F, PLGA, PEVA, PLA, PBMA, POE, PGA, PLLA, PAA, PEG, chitosan and/or derivatives of one or more of these polymers; however, other or additional polymers can be used. One or more polymer layers 310 are coated on the top of the one or more needles or micro-needles. As can be appreciated, layer 310 can also or alternatively be formed from one or more biological agents and/or adhesives. The one or more polymer layers 310 can include one or more polymers. Layer 310 can include one or more porous polymer and/or non-porous polymers. Layer 310 can include one or more biostable and/or biodegradable polymers. The one or more polymers can include, but are not limited to, parylene, parylene C, parylene N, parylene F, PLGA, PEVA, PLA, PBMA, POE, PGA, PLLA, PAA, PEG, chitosan and/or derivatives of one or more of these polymers; however, other or additional polymers can be used. The one or more polymers that form the layer 310 can be the same or different from the one or more polymers that form the one or more needles or micro-needles 300. Layer 310 can be used to 1) provide protection to the structure of the one or more needles or micro-needles 300, 2) at least partially control a rate of degradation of the one or more needles or micro-needles 300, and/or 3) at least partially control a rate of release of one or more biological agents on and/or in the one or more needles or micro-needles 300. As can be appreciated, layer 310 can have other or additional functions. The surface of the layer 310 can be or include one or more layers of one or more biological agents to provide a burst of biological agent in the interior of a body passageway and/or in the body passageway itself during and/or after insertion of the stent; however, this is not required. The one or more biological agents that can be used can include, but are not limited to, trapidil, trapidil derivatives, 5-Phenylmethimazole, 5-Phenylmethimazole derivatives, GM-CSF, GM-CSF derivatives, or combinations thereof; however other or additional biological agents can be used.

Referring now to FIG. 19, the base structure 40 of stent 20 includes one or more needles or micro-needles 350. The one or more needles or micro-needles are formed on the surface of the base structure. The one or more needles or micro-needles are formed from one or more biological agents and/or one or more polymer 360. A layer 362 of biological agent and/or polymer is also formed on the surface of the base structure. In one non-limiting example, the one or more needles or micro-needles 350 are formed from one or more biological agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In this non-limiting example, layer 362 is also formed from one or more biological agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, the one or more biological agents in layer 362 and forming the one or more needles or micro-needles 350 can be the same or different. The use of one or more biological agents to coat the top surface of the base structure and/or to form one or more needles or micro-needles can provide a burst of one or more biological agent in the treatment area (e.g., body passageway, etc.) after insertion of the stent. In another non-limiting example, the one or more needles or micro-needles 350 are formed from one or more biological agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In this non-limiting example, layer 362 is formed from one or more polymers. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers are non-porous polymers, the one or more non-porous polymers can include, but are not limited to, parylene C, parylene N, parylene F and/or a parylene derivative. The use of one or more biological agents to form one or more needles or micro-needles can provide a burst of one or more biological agent in the treatment area (e.g., body passageway, etc.) after insertion of the stent. In still another non-limiting example, the one or more needles or micro-needles 350 are formed from one or more polymers. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers are non-porous polymers, the one or more non-porous polymers can include, but are not limited to, parylene C, parylene N, parylene F and/or a parylene derivative. In this non-limiting example, layer 362 is formed from one or more biological agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The use of one or more biological agents to form layer 362 can provide a burst of one or more biological agent in the treatment area (e.g., body passageway, etc.) after insertion of the stent; however, this is not required.

Figure 20:
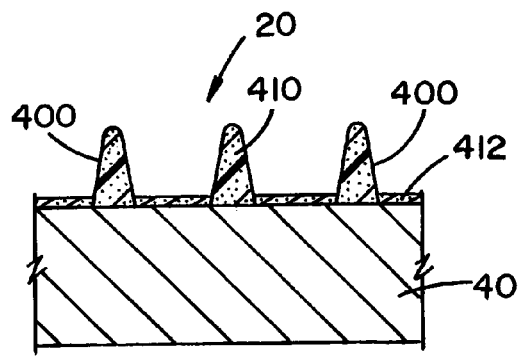
FIG. 20 is a cross-sectional view along line 3-3 of FIG. 2 illustrating micro-needles on the surface of the medical device that are formed of a biological agent and polymer.

Referring now to FIG. 20, the base structure 40 of stent 20 includes one or more needles or micro-needles 400. The one or more needles or micro-needles are formed on the surface of the base structure. The one or more needles or micro-needles are formed from one or more biological agents and one or more polymers 410. A layer 412 of biological agent and/or polymer is also formed on the surface of the base structure. As can be appreciated, the composition of layer 412 and forming the composition of the one or more needles or micro-needles 400 can be the same or different. In one non-limiting example, the one or more biological agents that at least partially form layer 412 and/or the one or more needles or micro-needles 400 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers that at least partially form layer 412 and/or the one or more needles or micro-needles 400 can include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that at least partially form layer 412 and/or the one or more needles or micro-needles 400 include a non-porous polymer to at least partially control a rate of release by molecular diffusion of the one or more biological agents that are mixed with the polymer. The inclusion of one or more biological agents in the one or more needles or micro-needles can provide controlled release of biological agent in the treatment area (e.g., body passageway, etc.) after insertion of the stent; however, this is not required. The use of one or more biological agents to form layer 412 and/or one or more needles or micro-needles 400 can provide a burst of one or more biological agent in the treatment area (e.g., body passageway, etc.) after insertion of the stent; however, this is not required.

Figure 19:
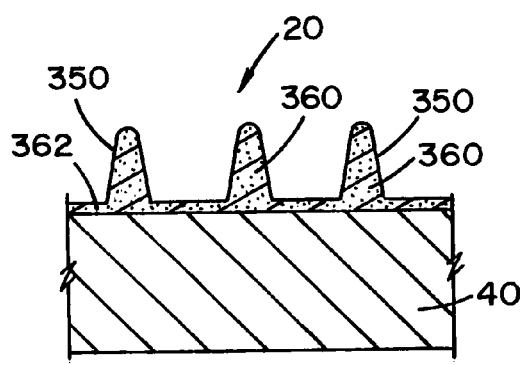
FIG. 19 is a cross-sectional view along line 3-3 of FIG. 2 illustrating micro-needles on the surface of the medical device that are formed of a biological agent.
Figure 21:
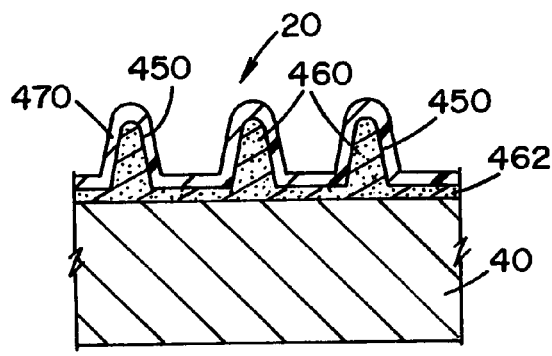
FIG. 21 is a cross-sectional view along line 3-3 of FIG. 2 illustrating micro-needles on the surface of the medical device that are formed of a biological agent and coated with a polymer.

Referring now to FIG. 21, FIG. 21 is a modification of the arrangement illustrated in FIG. 19. In FIG. 21, a coating 470, that is formed of one or more polymers and/or biological agents is placed over one or more needles or micro-needles 450 and layer 462. Specifically, the base structure 40 of stent 20 includes one or more needles or micro-needles 450. The one or more needles or micro-needles are formed on the surface of the base structure. The one or more needles or micro-needles are formed from one or more biological agents and/or polymers 460. A layer 462 of biological agent and/or polymer is also formed on the surface of the base structure. The composition of layer 462 and one or more needles or micro-needles can be the same or different. In one non-limiting example, the one or more biological agents that can at least partially form layer 462 and/or one or more needles or micro-needles 450 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers that can at least partially form layer 462 and/or one or more needles or micro-needles include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 462 and/or one or more needles or micro-needles 450 include one or more non-porous polymer such as, but not limited to, parylene C, parylene N, parylene F and/or a parylene derivative. The one or more non-porous polymers can be used to at least partially control a rate of release by molecular diffusion of the one or more biological agents in layer 462 and/or in the one or more needles or micro-needles 450; however, this is not required. Layer 470 that is coated on the top of the one or more needles or micro-needles and layer 462 includes one or more biological agents and/or polymers. In one non-limiting example, the one or more biological agents that can at least partially form layer 470 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In one non-limiting example, the one or more polymers that can at least partially form layer 470 include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers include one or more non-porous polymers, such non-porous polymer can include, but not limited to, parylene C, parylene N, parylene F and/or a parylene derivative. The one or more non-porous polymers can be used to at least partially control a rate of release by molecular diffusion of the one or more biological agents in layer 462, layer 470 and/or in the one or more needles or micro-needles 450; however, this is not required. When one or more biological agents at least partially form layer 470 and/or are coated on layer 470, not shown, the one or more biological agents can provide a burst of one or more biological agent in the treatment area (e.g., body passageway, etc.) after insertion of the stent; however, this is not required.

Figure 22:
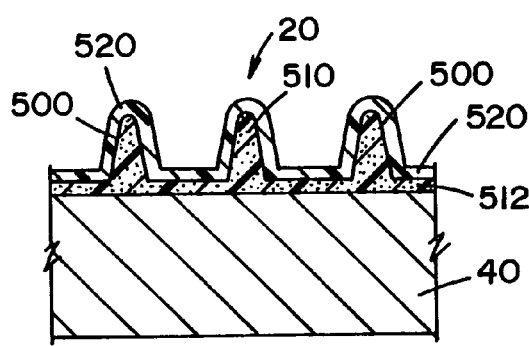
FIG. 22 is a cross-sectional view along line 3-3 of FIG. 2 illustrating micro-needles on the surface of the medical device that are formed of a biological agent and polymer and coated with a polymer.

Referring now to FIG. 22, FIG. 22 is a modification of the arrangement illustrated in FIG. 20. In FIG. 22, a coating 520, that is formed of one or more polymers and/or biological agents is placed over one or more needles or micro-needles 500 and layer 512. The composition of layer 520 and layer 512 and/or one or more needles or micro-needles can be the same or different. Specifically, the base structure 40 of stent 20 includes one or more needles or micro-needles 500. The one or more needles or micro-needles are formed on the surface of the base structure. The one or more needles or micro-needles are formed from a mixture of one or more biological agents and one or more polymers 510. A layer 512 of biological agent and polymer is also formed on the surface of the base structure. As can be appreciated, layer 512 and/or one or more needles or micro-needles 500 can be formed only of one or more polymers or one or more biological agents. The composition of layer 512 and one or more needles or micro-needles 500 can be the same or different. In one non-limiting example, the one or more biological agents that can at least partially form layer 512 and/or one or more needles or micro-needles 500 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers that can at least partially form layer 512 and/or one or more needles or micro-needles 500 include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 512 and/or one or more needles or micro-needles 500 include one or more non-porous polymers such as, but not limited to, parylene C, parylene N, parylene F and/or a parylene derivative. The one or more non-porous polymers can be used to at least partially control a rate of release by molecular diffusion of the one or more biological agents in layer 512 and/or in the one or more needles or micro-needles 500; however, this is not required. In one non-limiting example, the one or more polymers that can at least partially form layer 520 include one or more porous and/or non-porous polymers, and/or one or more biostable and/or biodegradable polymers. Non-limiting examples of one or more polymers that can be used include, but are not limited to, parylene, parylene C, parylene N, parylene F. PLGA, PEVA, PLA, PBMA, POE, PGA, PLLA, PAA, PEG, chitosan and/or derivatives of one or more of these polymers. When the one or more polymers include one or more non-porous polymers, such non-porous polymer can include, but not limited to, parylene C, parylene N, parylene F and/or a parylene derivative. The one or more non-porous polymers can be used to at least partially control a rate of release by molecular diffusion of the one or more biological agents in layer 512, layer 520 and/or in the one or more needles or micro-needles 500; however, this is not required. When one or more biological agents at least partially form layer 520 and/or are coated on layer 520, not shown, the one or more biological agents can provide a burst of one or more biological agent in the treatment area (e.g., body passageway, etc.) after insertion of the stent; however, this is not required.

Figure 23:
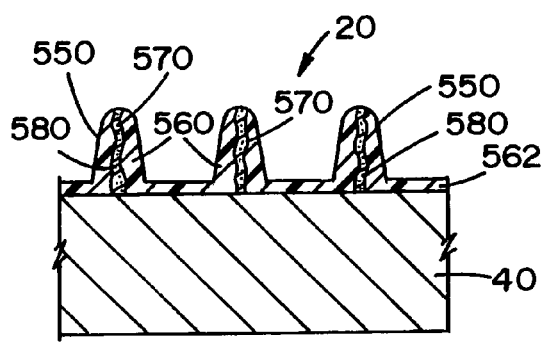
FIG. 23 is a cross-sectional view along line 3-3 of FIG. 2 illustrating micro-needles on the surface of the medical device that are formed of a polymer and includes an internal cavity that includes a biological agent; and, FIG. 24 is a cross-sectional view of a micro-needle on a that is penetrating into the inner surface of a body passageway or organ.

Referring now to FIG. 23, FIG. 23 is another modification of the arrangement illustrated in FIG. 20. In FIG. 23, one or more internal channels 570 are formed in one or more needles or micro-needles 550. The one or more internal channels 570 can include one or more biological agent and/or polymers. Specifically, the base structure 40 of stent 20 includes one or more needles or micro-needles 550. The one or more needles or micro-needles are formed on the surface of the base structure. The one or more needles or micro-needles are formed from one or more polymers and/or biological agents 560. A layer 562 of polymer and/or biological agent is also formed on the surface of the base structure. The composition of layer 562 and one or more needles or micro-needles can be the same or different. The one or more polymers that can at least partially form layer 562 and/or one or more needles or micro-needles 550 include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 562 and/or one or more needles or micro-needles 550 include one or more non-porous polymers such as, but not limited to, parylene C, parylene N, parylene F and/or a parylene derivative. The one or more non-porous polymers can be used to at least partially control a rate of release by molecular diffusion of the one or more biological agents in layer 562, in the one or more needles or micro-needles 550, and/or in one or more internal channels 570; however, this is not required. One or more of the needles or micro-needles 550 include an internal channel 570. The internal channel is illustrated as including one or more biological agents 580; however, it can be appreciated that one or more channels can include a mixture of one or more polymers and/or biological agents, or only one or more polymers. In one non-limiting example, the one or more biological agents includes trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The top opening of the channel enables delivery of one or more biological agents directly into treatment area (e.g., a wall of a body passageway or organ, etc.). The one or more biological agents in internal channel 570 can pass through and/or molecularly diffuse through the one or more polymers that at least partially form the one or more needles or micro-needles; however, this is not required. The release of the one or more biological agents through the one or more polymers that at least partially form the one or more needles or micro-needles can be a controlled or an uncontrolled release rate. As can be appreciated, a layer of biological agent, not shown, can be coated one or more needles or micro-needles 550. The layer of biological agent could include one or more biological agents. The placement of the layer of biological agent on the one or more needles or micro-needles 550 can provide a burst of one or more biological agents in the treatment area; however, this is not required. As can be appreciated, other combinations of polymer layer and/or layer of biological agent can be used on the stent. As can also or alternatively be appreciated, a layer of polymer, not shown, can be coated one or more needles or micro-needles 550. The layer of polymer could include one or more polymers. The placement of the layer of polymer on the one or more needles or micro-needles 550 can be used to a) at least partially control a release rate of one or more biological agents from the stent, and/or 2) provide structural support and/or protection to one or more needles or micro-needles. As can be appreciated, the polymer layer, when used, can have other or additional functions. These other combinations are also encompassed within the scope of the present invention.

Figure 24:
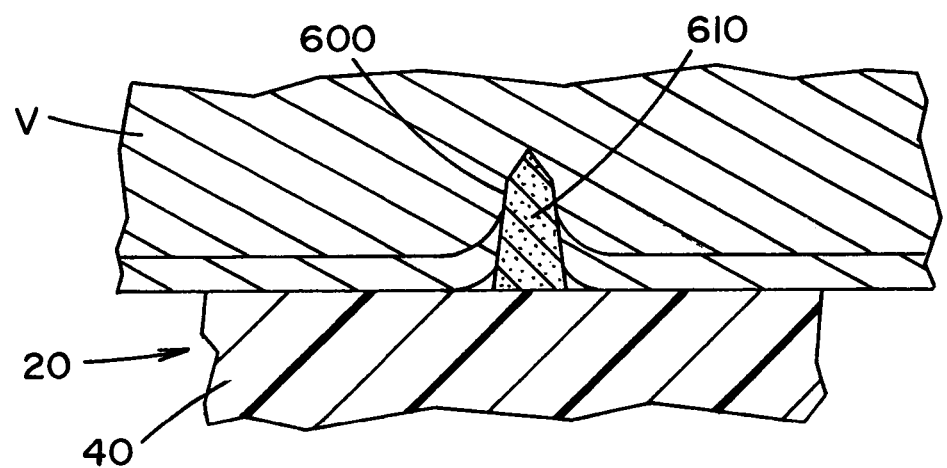

Referring now to FIG. 24, there is illustrated an enlarged portion of a surface of a stent 20 which includes a surface needle, micro-needle or other type of structure or micro-structure 600. The needle is shown to include at least one biological agent 610; however, the needle can also or alternatively include one or more polymers, adhesives, etc. The stent, when in the form of a stent, is illustrated as being in an expanded state. When the stent is inserted or expanded in a treatment area, the needle 600 on the outer surface of the stent engages and/or at least partially penetrates into blood vessel or organ V. When the needle includes one or more biological agents, the one or more biological agents are at least partially locally applied to a treatment area. This can be a significant advantage over system wide treatment with one or more biological agents. The locally treatment with one or more biological agent via the needle can more effectively and/or efficiently direct the desired agents to a treated area. The release of one or more biological agents from the needle can be controlled, if desired, to direct the desired amount of one or more biological agents to a treated area over a desired period of time. When the stent is expanded in a blood vessel, the one or more needles enable local delivery of one or more biological agents into the wall of the blood vessel. This local delivery is especially advantageous in large and/or thick blood vessels wherein system wide drug treatment is not very effective. In addition, the local delivery of biological agent by the needle directly into the blood vessel can be more effective than only releasing the biological agent from the surface of the stent since diffusion from the surface of the stent to the larger and/or thicker blood vessel may not be as effective as direct delivery by the needles to the blood vessel. The one or more needles on the stent surface can also or alternatively be used to facilitate in securing the stent to the treatment area during the expansion and/or insertion of the stent in a treatment area.

The various embodiment of the medical device set forth above represent a significant advancement over the current state of the art. The medical device includes or is formed of a biodegradable material. The biodegradable properties of one or more portions of the medical device enable the medical device to at least partially dissolve and/or be bodily absorbed after insertion in a patient. This feature is significant wherein the medical device is subject to repeated bending that can result in fracturing, micro-fracturing and/or braking of the medical device over time. The biodegradability of one or more portions of the medical device enables one or more portions of the damaged device to be remove without use of evasive surgical techniques. The biodegradability of the one or more portions of the medical device can also or alternatively enable the medical device to functions as a biological agent delivery device that deliveries one or more biological agents locally and/or systemically in a controlled or uncontrolled manner. The medical device when in the form of stent can be used to passivate vulnerable plaque in a body passageway. For instance, the medical device in the form of a stent can be designed so that a reduce amount of radial force is exerted in a body passageway after the stent has been expanded. The reduced amount of radial force applied by the stent can reduce the amount of vulnerable plaque that become dislodged from the body passageway. The dislodgement of plaque can result in blockage of the body passageway upstream from the inserted stent. The stent is maintained in place in the body passageway by frictional content between the wall of the body passageway and the expanded stent. The one or more biological agents coated on and/or contained in the stent can be selected to slowly remove the plaque from the treated area. As can be appreciated, the one or more polymers on the medical device can be naturally biodegradable or become biodegradable or more biodegradable upon a certain event (e.g., exposure to electromagnetic radiation, etc.). Likewise, the one or more biological agents can be naturally active or be activated upon a certain event (e.g., exposure to electromagnetic radiation, etc.). Furthermore, the one or more biological agents can be naturally soluble or become soluble upon a certain event (e.g., exposure to electromagnetic radiation, etc.).

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A method of reducing stent strut fracture problems that can result from repeated bending of said stent in a body passageway comprising:
   a. selecting a stent having a body portion, said body portion having an unexpanded and expanded cross-section area, a majority of said body portion at least partially formed of biodegradable polymer so as degrade over time when exposed to fluids in the body passageway to thereby remove itself from a treatment site in said body passageway, said body portion includes at least one cavity, said cavity at least partially filled with a biological agent;
   b. positioning said stent at said treatment site of said body passageway;
   c. expanding said body portion of said stent in said body passageway to said expanded cross-sectional area; and,
   d. allowing said body portion of said stent to flex in said body passageway such that continual flexing of said body portion results in at least one fracture in said body portion, said fracturing of said body portion resulting in accelerated degradation of said body portion at the site of said fracture thereby causing accelerated absorption of said body portion in said body passageway.

2. The method as defined in claim 1, wherein said biodegradable polymer is at least partially coated with a non-biodegradable polymer.

3. The method as defined in claim 1, wherein an outer surface of said body portion includes a plurality of said micro-structures, said plurality of said micro-structures extending outwardly from said outer surface of said body portion, said plurality of said micro-structures including biodegradable polymer, biological agent, or combinations thereof.

4. The method as defined in claim 3, wherein said plurality of said micro-structures include said biological agent, said plurality of said micro-structures designed to at least partially penetrate into or depress on an inner surface of a body passageway when said body portion is expanded to said expanded cross-sectional area at said treatment site of said body passageway so as to result in local delivery said biological agent into a wall of said body passageway, on a localized region on a wall of said body passageway, or combinations thereof.

5. The method as defined in claim 4, wherein said plurality of said micro-structures include a cavity at least partially formed by said biodegradable polymer, said cavity at least partially filled with said biological agent.

6. The method as defined in claim 5, wherein said cavity in said body portion is connected to said cavity in said plurality of said micro-structures.

7. The method as defined in claim 6, wherein said body portion includes biological agent on said outer surface of said body portion, said biological agent on said outer surface different from said biological agent in said cavity.

8. The method as defined in claim 7, wherein said biological agent on said outer surface of said body portion, in said cavity or combinations thereof is formulated to at least partially inhibit re-narrowing of the vessel diameter, inhibit thrombosis, facilitate endothelium generation, create an integral endothelial layer, or combinations thereof.

9. The method as defined in claim 5, wherein polymer coats a portion of said plurality of said micro-structures to encapsulate said biological agent in said cavity of said plurality of said micro-structures, said polymer including a biodegradable polymer, a biostable polymer, or combinations thereof.

10. The method as defined in claim 3, wherein plurality of said micro-structures include biological agent, said biological agent includes one or more agents selected from the group consisting of trapidil, trapidil derivatives, taxol, taxol derivatives, cytochalasin, cytochalasin derivatives, paclitaxel, paclitaxel derivatives, rapamycin, rapamycin derivatives, GM-CSF and GM-CSF derivatives.

11. The method as defined in claim 3, wherein said biodegradable polymer includes one or more polymers selected from the group consisting of chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG and a PEG derivative , or combinations thereof.

12. The method as defined in claim 3, wherein said body portion includes a radiopaque marker material, said radiopaque marker distributed throughout said body portion of said stent, or a certain location on said body portion of said stent.

13. The method as defined in claim 3, wherein said biological agent imparted to said body portion of said stent by spray coating, dip coating, roll coating, sonication, brushing, plasma deposition, depositing by vapor deposition, or combinations thereof.

14. The method as defined in claim 1, wherein said biological agent includes one or more agents selected from the group consisting of trapidil, trapidil derivatives, taxol, taxol derivatives, cytochalasin, cytochalasin derivatives, paclitaxel, paclitaxel derivatives, rapamycin, rapamycin derivatives, GM-CSF and GM-CSF derivatives.

15. The method as defined in claim 14, wherein said biodegradable polymer includes one or more polymers selected from the group consisting of chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, and a PEG derivative.

16. The method as defined in claim 15, wherein at least one polymer coats a portion of a plurality of said micro-structures to cause said biological agent in said cavity of said plurality of micro-structures to be encapsulated in said cavity, said at least one polymer including a biodegradable polymer, a biostable polymer, or combinations thereof.

17. The method as defined in claim 16, wherein said outer portion of said body portion includes said biological agent, said biological agent on said outer surface different from said biological agent in said cavity of said plurality of micro-structures.

* * * * *